(12) United States Patent
Pendleton et al.

(10) Patent No.: US 10,485,683 B2
(45) Date of Patent: *Nov. 26, 2019

(54) TELESCOPING URETERAL STENT

(71) Applicant: Cook Medical Technologies LLC, Bloomington, IN (US)

(72) Inventors: Steven L. Pendleton, Spencer, IN (US); Gary L. Neff, Bloomington, IN (US); Benjamin T. Biltz, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/917,093

(22) Filed: Mar. 9, 2018

(65) Prior Publication Data
US 2018/0193174 A1    Jul. 12, 2018

Related U.S. Application Data

(63) Continuation of application No. 14/615,032, filed on Feb. 5, 2015, now Pat. No. 9,937,067.
(Continued)

(51) Int. Cl.
*A61F 2/852* (2013.01)
*A61M 27/00* (2006.01)
(Continued)

(52) U.S. Cl.
CPC ........... *A61F 2/852* (2013.01); *A61M 27/008* (2013.01); *A61F 2/95* (2013.01); *A61F 2002/047* (2013.01); *A61F 2002/048* (2013.01); *A61F 2220/0025* (2013.01); *A61F 2220/0033* (2013.01); *A61F 2230/0004* (2013.01); *A61F 2230/0067* (2013.01); *A61F 2250/001* (2013.01); *A61F 2250/006* (2013.01); *A61F 2250/0007* (2013.01); *A61F 2250/0008* (2013.01); *A61F 2250/0012* (2013.01); *A61F 2250/0021* (2013.01); *A61F 2250/0029* (2013.01); *A61F 2250/0039* (2013.01); *A61F 2250/0065* (2013.01); *A61F 2250/0098* (2013.01)

(58) Field of Classification Search
CPC ...... A61F 2002/048; A61F 2/852; A61F 2/95; A61M 27/008
See application file for complete search history.

(56) References Cited

U.S. PATENT DOCUMENTS 5,064,435 A * 11/1991 Porter ................. A61F 2/90
606/151
6,508,789 B1 * 1/2003 Sinnott ............. A61M 25/0097
604/164.01
(Continued)

*Primary Examiner* — William H Matthews
(74) *Attorney, Agent, or Firm* — Brinks Gilson & Lione

(57) ABSTRACT

An indwelling stent is provided. The stent includes a distal member that extends between a distal end portion and a proximal end portion and defines a lumen therethrough, and a proximal member that extends between a distal end portion and a proximal end portion and defines a lumen therethrough, wherein the distal member and the proximal member collectively define the stent, and wherein the distal and proximal members are discrete components and are telescopingly arranged with the distal end portion of the proximal member extending over an outer surface of the distal member.

18 Claims, 19 Drawing Sheets

Related U.S. Application Data

(60) Provisional application No. 61/937,165, filed on Feb. 7, 2014.

(51) Int. Cl.
    *A61F 2/04*         (2013.01)
    *A61F 2/95*         (2013.01)

(56) References Cited

U.S. PATENT DOCUMENTS

| | | | |
|---|---|---|---|
| 9,937,067 B2 * | 4/2018 | Pendleton | A61F 2/852 |
| 2001/0047164 A1 * | 11/2001 | Teague | A61M 25/04 |
| | | | 604/525 |
| 2002/0188246 A1 * | 12/2002 | Hayner | A61M 25/0017 |
| | | | 604/48 |
| 2003/0004496 A1 * | 1/2003 | Tanghoj | A61M 25/0009 |
| | | | 604/544 |
| 2005/0113905 A1 * | 5/2005 | Greenberg | A61F 2/07 |
| | | | 623/1.16 |
| 2008/0097394 A1 * | 4/2008 | Lampropoulos | A61M 25/0147 |
| | | | 604/524 |

\* cited by examiner

TELESCOPING URETERAL STENT

CROSS-REFERENCE TO RELATED APPLICATIONS

This application is a continuation of U.S. patent application Ser. No. 14/615,032, filed on Feb. 5, 2015, issued as U.S. Pat. No. 9,937,067 on Apr. 10, 2018, which claims priority from U.S. Provisional Patent Application 61/937,165 filed on Feb. 7, 2014, the entirety of each are hereby fully incorporated by reference herein.

TECHNICAL FIELD

This disclosure relates to indwelling stents, such as ureteral stents that are used to maintain patency between a patient's kidney and bladder in clinical situations.

BRIEF SUMMARY

A first representative embodiment of the disclosure is provided. The first embodiment includes an indwelling stent. The stent includes a distal member that extends between a distal end portion and a proximal end portion and defines a lumen therethrough, and a proximal member that extends between a distal end portion and a proximal end portion and defines a lumen therethrough. The distal member and the proximal member collectively define the stent, and the distal and proximal members are discrete components and are telescopingly arranged with the distal end portion of the proximal member extending over an outer surface of the distal member.

A second representative embodiment of the disclosure is provided. The embodiment includes a system of deploying an indwelling stent. The system includes a stent formed form a distal member that extends between a distal end portion and a proximal end portion and defines a lumen therethrough, and a proximal member that extends between a distal end portion and a proximal end portion and defines a lumen therethrough. The distal member and the proximal member collectively define the stent, and wherein the distal and proximal members are discrete components and are telescopingly arranged with the distal end portion of the proximal member extending over an outer surface of the distal member. A first pusher extends between distal and proximal ends with a lumen therethrough, and a second pusher that extends between a distal tip and proximal tip and is disposed through the lumen of the first pusher and the lumen of the proximal member with the distal tip of the second pusher contacting the proximal end portion of the distal member.

Other embodiments of the disclosure will become apparent in view of the following description taken in connection with the accompanying drawings.

DETAILED DESCRIPTION OF THE DRAWINGS AND THE PRESENTLY PREFERRED EMBODIMENTS

Figure 5:
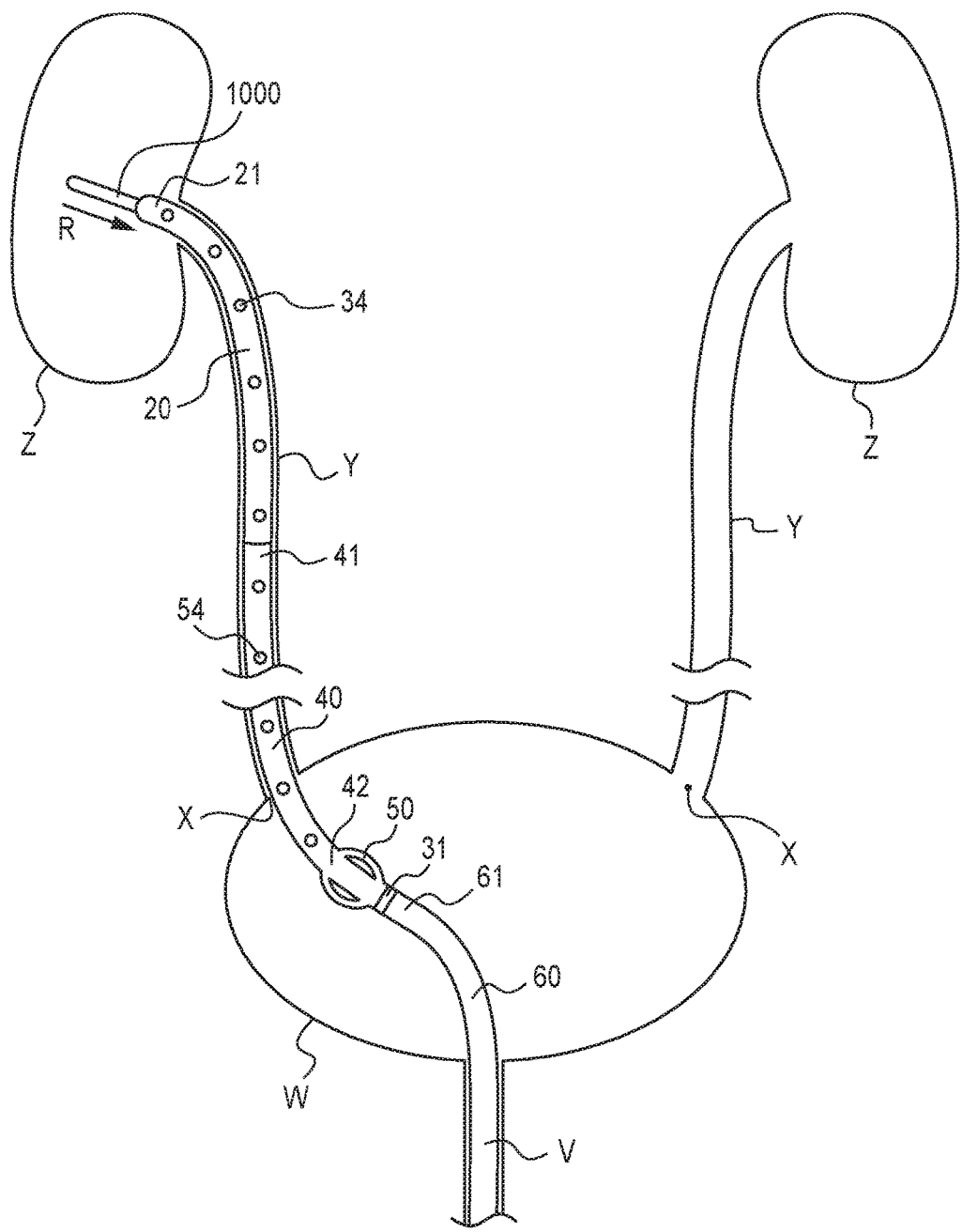
FIG. 5 is a simplified view of a portion of a urinary system, showing the system of FIG. 3 deploying a distal end portion of an indwelling stent into a patient's kidney.
Figure 6:
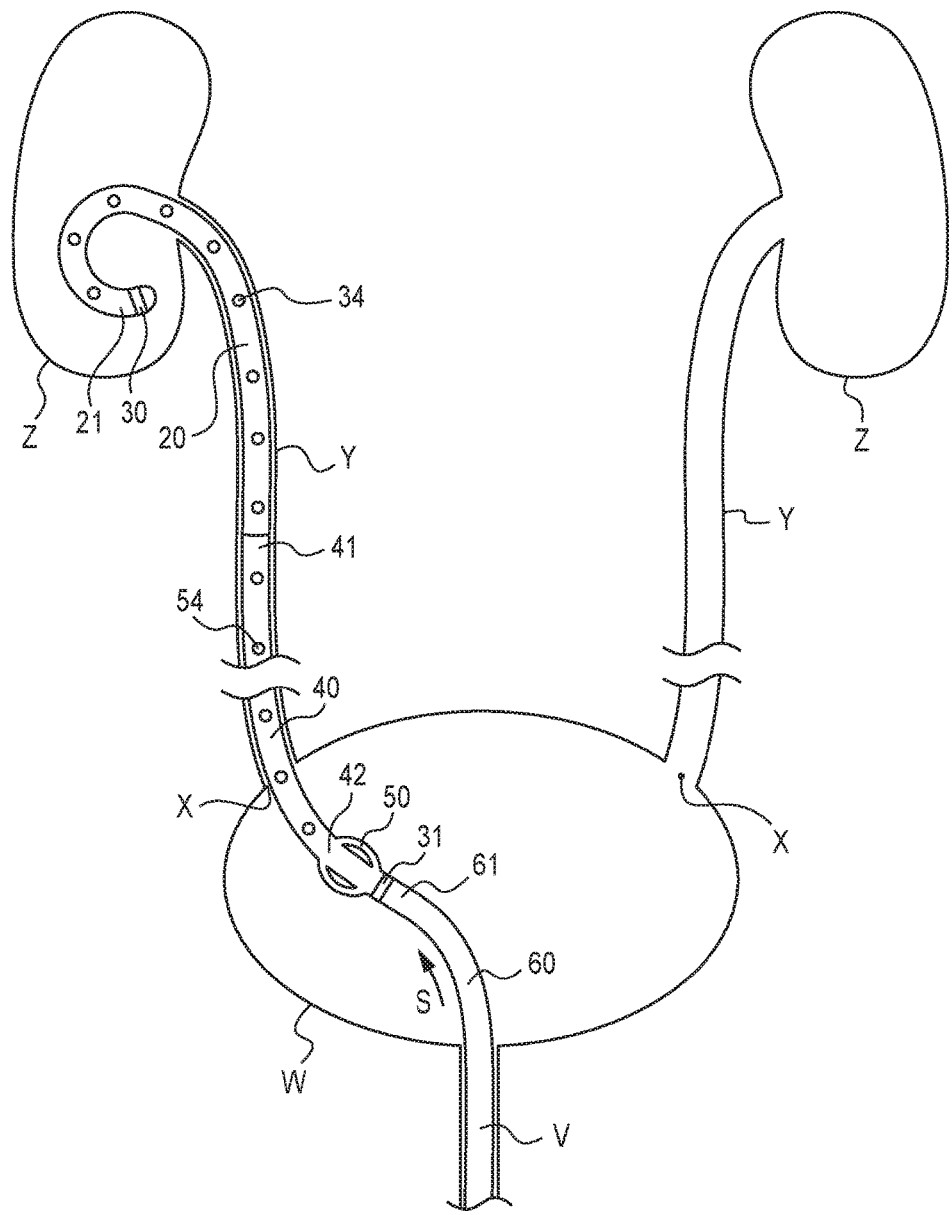
FIG. 6 is the view of FIG. 5 showing a pigtail on the distal end portion of the distal member of the indwelling stent disposed within a kidney, with a wire guide withdrawn from the distal end portion.

Turning now to FIGS. 1-16, an indwelling stent 10 is provided. The indwelling stent 10 is depicted and described herein as specifically suitable for deployment within a ureter (Y, FIGS. 5-7) of a patient (such as a human or a mammal), and specifically extending from just outside of a patient's UVJ (X) (ureterovesical junction) and into a patient's kidney (Z). Indwelling stents for use in a ureter are commonly indicated for patients where there is a concern regarding current or potential future blockage of urine flow through the ureter (either completely or partially) due to stenosis or strictures, or other causes, which prevents normal urine flow from the kidney and into the bladder or other complications, as well as other clinical indications. While the stent 10 is specifically described herein for use within a patient's ureter Y between the UVJ and the kidney, those of ordinary skill in the art will appreciate, after a thorough review and understanding of this disclosure, that the stent 10 and the system 300 for delivering the stent 10 discussed herein (as well as the method for delivery disclosed herein) may be conveniently and successfully used and deployed within other luminal parts of the anatomy that may benefit from receiving a stent or other implantable tubular structure. For example, a patient's vascular system, arterial system, gastrointestinal system, biliary tree, or other luminal portions of the anatomy may receive the indwelling stent 10 described herein with only modification that would be readily understood and appreciated by those of skill in the art after a thorough review of this specification.

Figure 1:
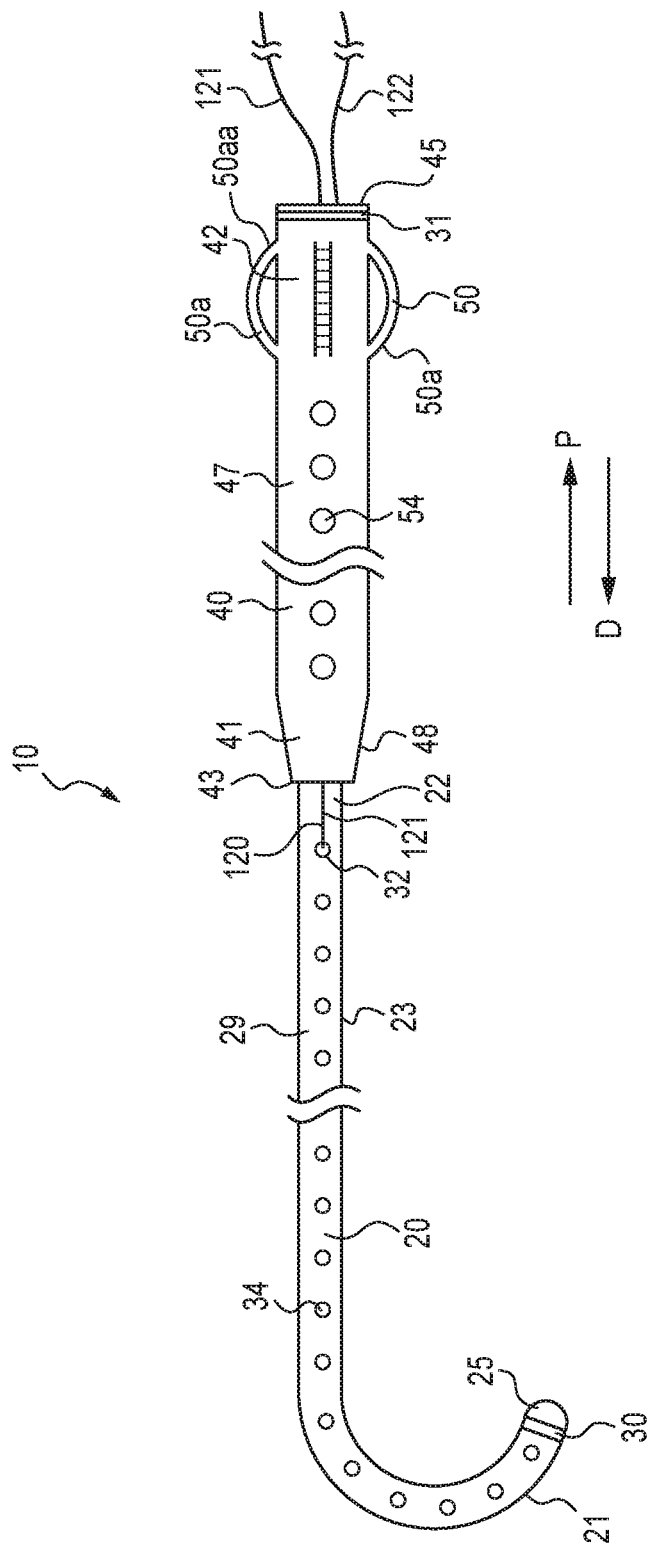
FIG. 1 is a side view of an indwelling stent.
Figure 2:
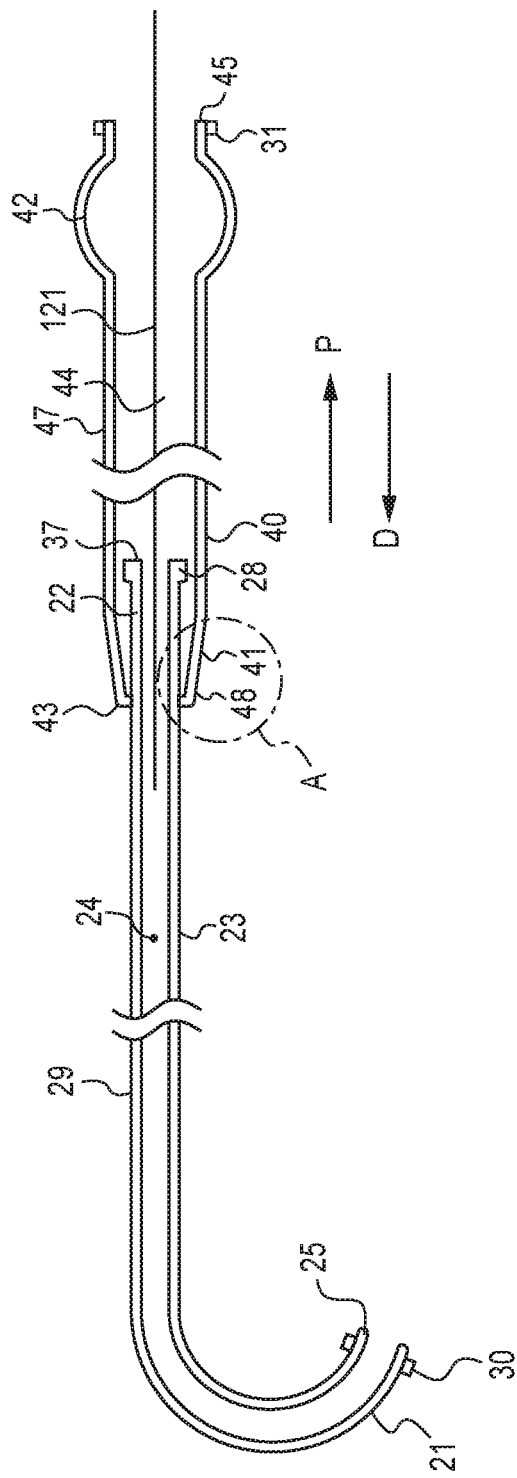
FIG. 2 is a cross-sectional view of the indwelling stent of FIG. 1.

FIGS. 1 and 2 depict an indwelling stent 10 that is suitable for deployment within a ureter and between a patient's kidney and bladder. The stent 10 is formed with a distal member 20 and a proximal member 40 that are telescopingly disposed with respect each other. The distal member 20 is formed between a distal end portion 21 and a proximal end portion 22 with a lumen 24 disposed therethrough allowing communication through the distal member 20. The proximal member 40 is formed between a distal end portion 41 and a proximal end portion 42 with a lumen 44 disposed therethrough allowing communication through the proximal member 40. The distal and proximal members 20, 40 may be formed as discrete components and may be separable.

The distal and proximal members 20, 40 are disposed such that an overall length of the stent 10, between a distal tip 25 of the distal member 20 and a proximal tip 45 of the proximal member 40, can be varied as needed by adjusting the relative position of the proximal member 40 with respect to the distal member 20. In some embodiments, the proximal member 40 is arranged to telescopingly slide outside of the outer surface 23 of the distal member, with a distal end portion 41 of the proximal member 40 disposed over the proximal end portion 22 of the distal member 20, such that the proximal end portion 22 of the distal member 20 extends through a portion of the lumen 44 of the proximal member 40. The proximal member 40 may also enclose a central portion of the distal member 20 disposed between the distal and proximal end portions 21, 22.

In some embodiments, the distal member 20 (not including the length of the arcuate distal end portion 21) may be between about 10 cm and about 30 cm (inclusive of the various lengths within this range), and in some embodiments the distal member 20 may be within a range of between about 21 cm and 27 cm (inclusive of all lengths within this range). In some embodiments, the outer diameter of the distal member 20 may be within a range of between 3 French and 10 French (inclusive of all diameters within this range), and may be at an outer diameter of about 6 French in some embodiments. The inner diameter of the distal portion 20 may be a suitable diameter that is based upon the necessary material thickness of the inner member 20. A smallest inner diameter of the distal member 20 may be about 0.035 inches, with this inner diameter or larger being suitable. In embodiments where the stent 10 may be used for other clinical applications, the length and diameter of the distal member 20 may fall within different ranges that are suitable for that part of the anatomy, such as, by way of example only, a range of outer diameter between 3 and 20 French (inclusive of all diameters within this range). As with the other dimensions presented herein for potential application within a ureteral indwelling stent, one of ordinary skill in the art will understand that the various dimensions for stents that are for other clinical applications may be different than presented herein based upon the sizes of the anatomy and the requirements to provide a stent that is suitable for that clinical anatomy.

The proximal member 40 may be about 3 to about 15 cm (inclusive of the various lengths within this range), and in some embodiments the proximal member 40 may be within a range of between about 6 to about 9 cm (inclusive of all lengths within this range). In some embodiments, the outer diameter of the proximal member 40 may be within a range of between 4 French and 11 French (inclusive of all diameters within this range), and may be at an outer diameter of about 7 or 8 French in some embodiments. In exemplary embodiments used for other clinical indications, the outer diameter of the proximal member 40 may be between 4 and 21 French (inclusive of all diameters within this range) or another clinically suitable range. The inner diameter of the proximal portion 40 may be a function of the wall thickness and the desired outer diameter of the proximal portion 40, as well as a function of the outer diameter of the distal portion 20. The length of a typical ureter is about 12 inches (25 mm), and as discussed herein, the lengths of the distal and proximal members 20, 40 are chosen to allow the stent 10 to traverse the ureter and minimize the amount of the proximal end portion 42 that extends into the bladder. The inner diameter of a typical ureter is about 3-4 mm (9-12 French), and therefore the outer diameter of the proximal member 40

(and therefore the other dimensions that are a function of this OD) is based upon establishing a good fit through the ureter.

In some embodiments, the distal end portion 21 of the distal member 20 may be biased into an arcuate configuration, such as a partial pigtail (FIG. 1), a complete loop or pigtail, a corkscrew, or helix or another arcuate structure. The distal member 20 may be formed such that its distal end portion is urged into one of the geometries mentioned above, or another non-linear geometry, that is adapted to retain the distal end portion 21 within a patient's kidney and prevent the stent 10 from being displaced out of the kidney and proximally through the ureter toward the bladder after deployment. The distal end portion 21 may be sufficiently flexible such that it can be straightened, such as with a wire guide 1000 (FIG. 3) disposed through the lumen 24 of the distal member 20, when the stent 10 is being translated through the patient's urethra (V, FIGS. 5-7), ureter, and ultimately into the patient's kidney. The distal end portion 21 can also be straightened from the biased arcuate configuration when the distal member 20 is pulled proximally, either by pulling upon the proximal member 40 (which then pulls upon the distal member 20 due to the engagement between the proximal and distal members 40, 20 as discussed below), or by pulling on a flexible member 120, such as a length of suture, that may be threaded with respect to the distal member 20 and extend out of the patient.

As mentioned elsewhere herein, the proximal member 40 is telescopically coupled with the distal member 20 such that the proximal member 40 may be slidable over the outer surface 23 of the distal member 20 and covers all or a portion of the proximal end portion 22 of the distal member 20. The proximal member 40 may be further telescopically slid over the distal member 20 such that the proximal member 40 covers a significant portion of the length of the distal member 20. The slidable telescopic relationship between the proximal member 40 and the distal member 20 allows the stent 10 to be initially positioned with a relatively long length, such that at least the proximal end portion 42 of the proximal member 40 extends through the UVJ and into the bladder when the distal end portion 21 of the distal member 20 is disposed within the kidney.

In other embodiments, the distal member 20 may be telescopically slid over the proximal member 40. In both of these embodiments, the lumen of the distal member 20 and the lumen of the proximal member 40 are arranged in communication with each other such that the lumens of both of the distal and proximal members 20, 40 establish a continuous path through the entire length of the stent, and between the distal end portion of the distal member 20 and the proximal end portion of the proximal member 40 of the stent.

Figure 7:
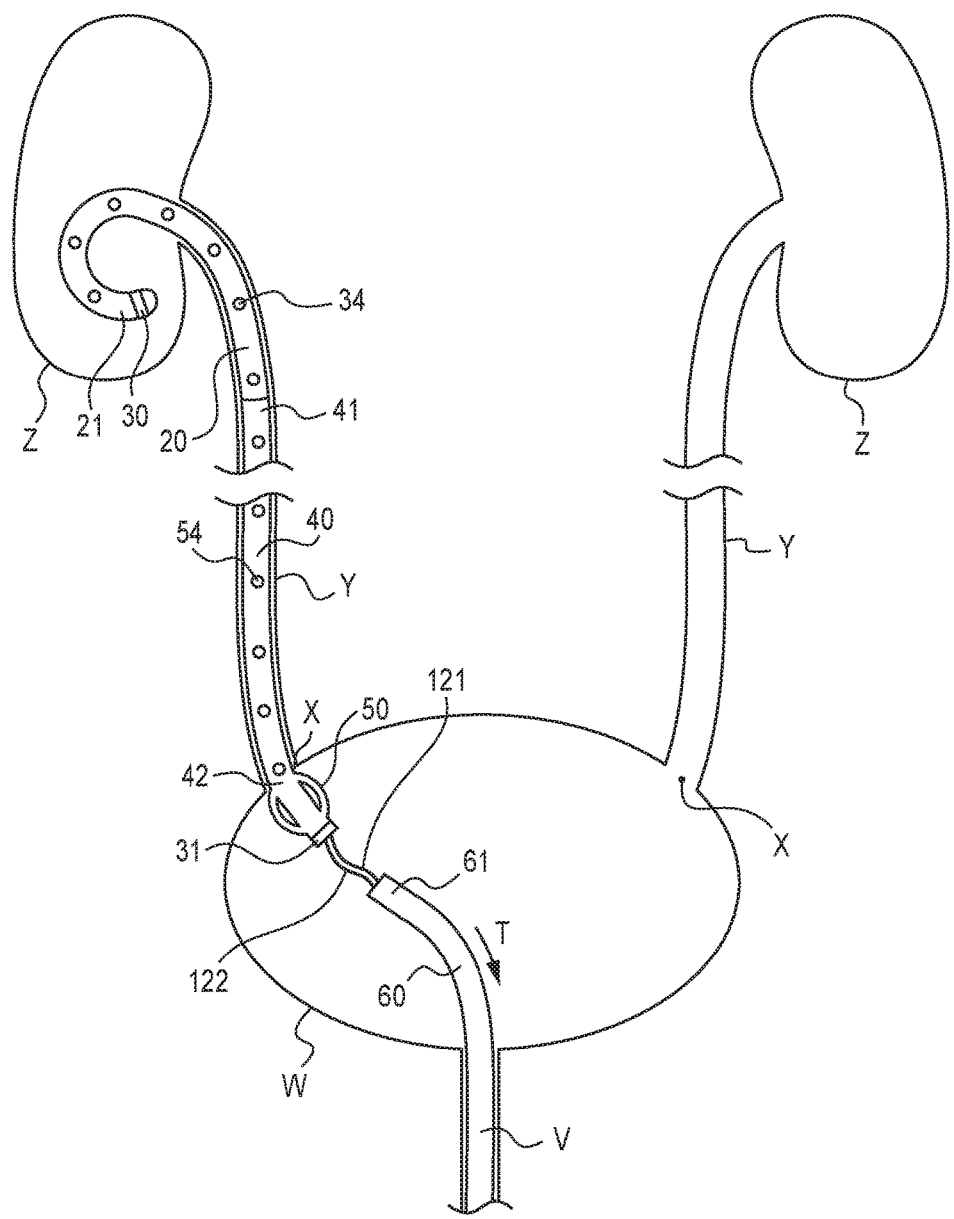
FIG. 7 is the view of FIG. 5 showing the enlarged portion of the proximal member disposed at the UVJ (ureterovesical junction) of a patient and the first and second pushers withdrawn from the stent.

When the stent 10 is correctly positioned within the kidney and through the ureter and into the bladder the proximal member 40 may be urged distally (as described in more detail below) with respect to the distal member 20 such that the overall length of the stent 10 decreases. The proximal member 40 may be urged distally until an enlarged portion 50 of the proximal end portion 42 is placed in proximity or in contact with the UVJ (FIG. 7). As discussed in more detail below, the enlarged portion 50 may be constructed to be larger (at least in one dimension) than a patient's UVJ such that the enlarged portion 50 is mechanically prevented from entering into the UVJ and therefore into the patient's ureter. In other embodiments, the proximal member 40 may be formed without an enlarged portion (as discussed herein) such that the proximal end portion 42 is at the same outer diameter as the remaining tubular portions of the proximal member 40 (not including any differing outer diameter of the distal end portion 41 as discussed herein).

The enlarged portion 50 may be one of many different structures that are sized to extend radially to a larger diameter than the UVJ and the ureter such that the enlarged portion 50 and any portion of the proximal member 40 that is proximal of the enlarged portion 50 does not pass through the UVJ and enter the ureter. In some embodiments, the enlarged portion 50 may include one or more portions that extend (in at least one direction, and in some embodiments multiple or all directions) to a larger diameter than a smallest diameter of the UVJ and ureter. In some embodiments, the enlarged portion 50 may be fixed at the extended enlarged diameter, and may be formed as a bulb 50*d* (FIG. 13), a tube, or another structure that is larger (in at least one diameter or section) than the UVJ and the inner diameter of the ureter.

In other embodiments, the enlarged portion 50 may be a structure that is biased, or is trained to extend, into an extended configuration that includes at least one (some, or all) diameter(s) or portions that is larger than the smallest diameter of the UVJ and ureter or a corresponding portion of the UVJ and ureter. As shown in FIGS. 1-4, the enlarged portion 50 may be formed with a plurality of extendable arms 50*a*, such as malecot arms, or alternatively arms that are only attached to the proximal member 40 at one end. The arms 50*a* may be biased to extend outward into an extended position as shown in the figures, with the extended position configured to be larger than the smallest diameter, or section, or otherwise be larger than the UVJ and the ureter.

In some embodiments, the malecot arms 50*a* are configured to extend to a diameter between about 3-20 mm (inclusive of all values within this range), and more particularly about 6, 7, 8, 9, or 10 mm. In some embodiments, a small value for the size of the malecot arms 50*a* is preferred, which will be larger than the UVJ, to minimize intrusion into the bladder and potential rubbing against the walls of the bladder. The malecot arms 50*a* may be any suitable length, and specifically a length to provide adequate strength to the arms (in the biased outward position), but to also minimize the size of the proximal end portion 42 that extends into the bladder. In some embodiments, the malecot arms 50*a* may be a range of about 2 mm to about 20 mm (including all values within this range), and in some embodiments the arms may be 5, 7, or 10 mm. In some embodiments, 4 malecot arms 50*a* may be provided (equally or non-equally spaced around the circumference of the proximal end portion 42), while other numbers of arms, such as 2 (FIGS. 17, 20-22), 3, 5, 6, or more may be provided.

The arms 50*a* are configured to be compressible toward or to the outer diameter of the remaining portion of the proximal end portion 42, to allow for ease of initial deployment through the urethra and removal from the patient when the stent 10 is no longer needed or needs to be replaced. In some embodiments, the arms 50*a* may be compressed to substantially the same outer diameter as a portion of the proximal member 40, such as a central portion of the proximal member 40 (i.e. proximal of the distal end portion 41 of the proximal member 40). The term substantially the same is defined herein to be equal to the outer diameter or a diameter that is within ranges of plus or minus 5%, or 10%, or 20% of the nominal outer diameter. The arms 50*a* may be compressible with an external force placed thereon, such as by forceps, a grasper, a basket, or the like, or in other embodiments, the arms 50*a* may be compressible when the proximal ends 50*aa* (FIG. 1) engage tissue (such as the urethral sphincter) which compresses the arms 50*a* toward the remainder of the outer surface 43 of the proximal end portion 42 for withdrawal from the patient through the urethra.

Figure 17:
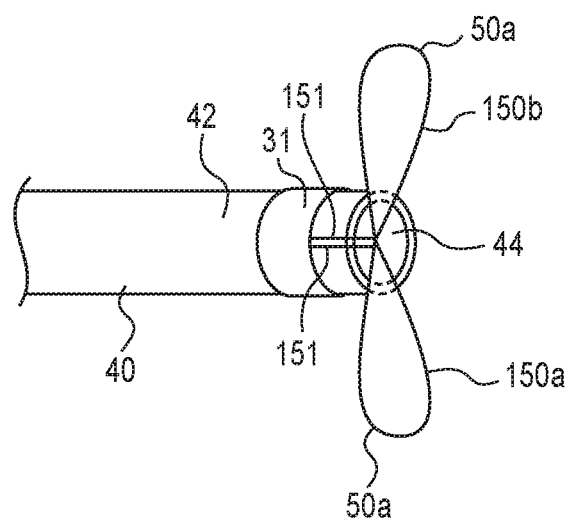
FIG. 17 is a perspective view of another embodiment of a proximal end portion of the proximal member that is usable with the stent of FIG. 1, with the arms in the deployed configuration.
Figure 18:
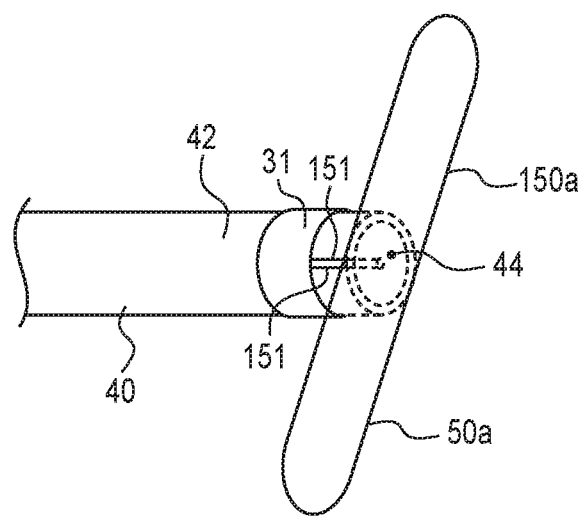
FIG. 18 is a perspective view of another embodiment of a proximal end portion of the proximal member that is usable with the stent of FIG. 1, with the arms in the deployed configuration.
Figure 18A:
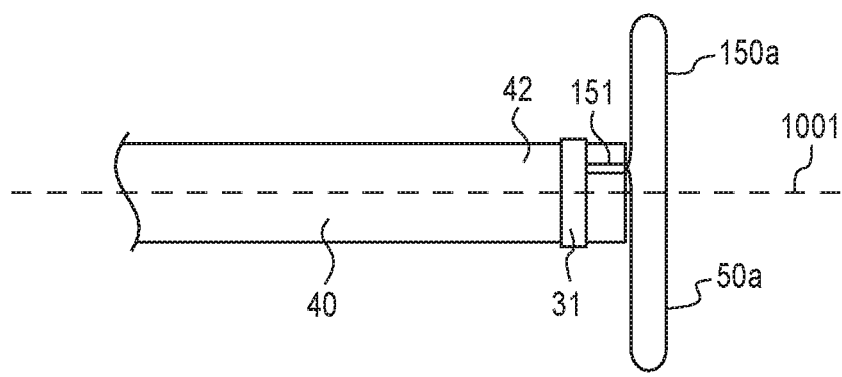
FIG. 18a is a side view of the embodiment of FIG. 18.

In some embodiments, as shown in FIGS. 17-18a, the malecot arms 50a may be made from only wires, such as nitinol wires or other elastic or superelastic material. As shown in FIGS. 18 and 18a, the malecot arms 50a may include a single loop 150a that is biased to extend as a loop that is generally directed radially outward from the proximal member 40 and in directions that are generally perpendicular to the longitudinal axis 1001 through the proximal member. The term "generally perpendicular" is defined herein to include both exactly perpendicular as well as angles that are up to 5 degrees from the exact perpendicular in any direction.

Figure 17A:
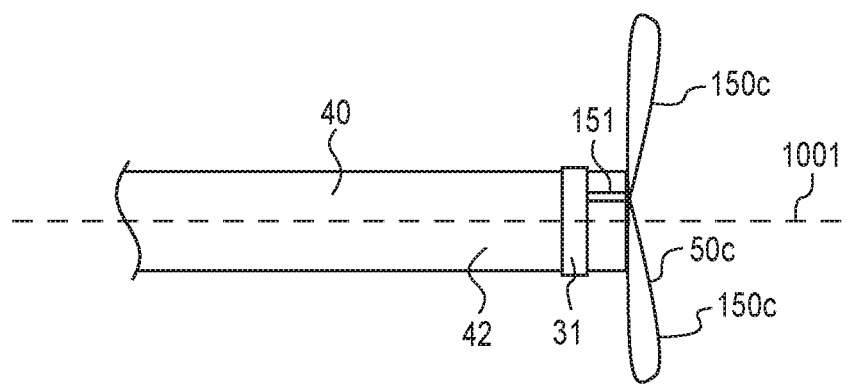
FIG. 17a is a side view of the embodiment of FIG. 17.
Figure 19A:
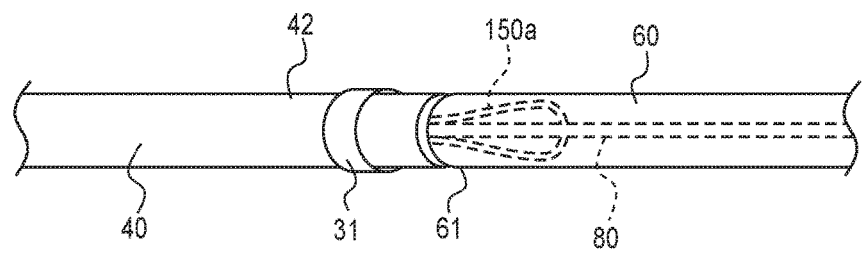
FIG. 19a is a perspective view of the second pusher disposed through the proximal end portion of FIG. 17, with the proximal end portion disposed within the first pusher and the first pusher proximate to the proximal member of the stent.
Figure 19B:
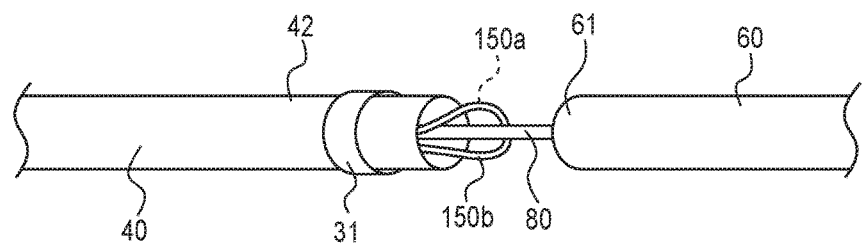
FIG. 19b is the view of FIG. 19a with the proximal end portion released from the first pusher and the first pusher pulled away from the proximal member of the stent.

In other embodiments shown in FIGS. 17 and 17a, the malecot arms 50a may form two or more loops 150c that extend radially outward from the proximal member 40 and in directions that are generally perpendicular, similar to the embodiment shown in FIGS. 18-18a. In some embodiments shown in FIGS. 19a and 19b, the malecot arms 50a made from wires (whether only wires, or wires that are fixed to other materials as described elsewhere herein) may be disposed such that the loops 150c (or the single loop 150a) formed by the wires extend around the second pusher 80 (discussed below) when present. In some embodiments as shown in FIG. 19a, the loop(s) 150a may extend within the lumen of the first pusher 60 (discussed below) and around the outer surface of the second pusher 80. The wires are configured to be urged toward the extended position when released from the lumen of the first pusher 60.

In other embodiments, the malecot arms 50a may be made from the same material(s) as the proximal portion 40 of the stent. In some embodiments, the malecot arms 50a may be made from the material(s) that forms the proximal member 40 of the stent (or at least the proximal end portion 42 of the proximal member 40 of the stent) in combination with a wire, such as superelastic wire as discussed above, which may be layered with the material(s), co-extruded with the material(s), or embedded within the material(s) or by another method that would be understood to one of ordinary skill in the art after a thorough review of this specification.

In embodiments where the malecot arms 50a are formed from wires (either wires only, or wires in combination with the material(s) forming the proximal member), the wires may be fixed to the proximal end portion 42 of the second member 40. In some embodiments, the proximal end portion 42 may include a ring 31, such as a ring that forms an echogenic or radiopaque portion, as best shown in FIGS. 17-18a. The ring 31 may be press-fit to the proximal end portion 42 or may be fixed with adhesive or by another means. In embodiments, one or both ends 151 of the wire that forms the arms 50a of the malecot (either alone or in combination with other materials) may be disposed between the material forming the proximal end portion 42 and the ring 31 (or otherwise fixed to the proximal end portion 42 of the second member 40 with the ring 31) and therefore supported and retained in place in this manner.

Figure 20:
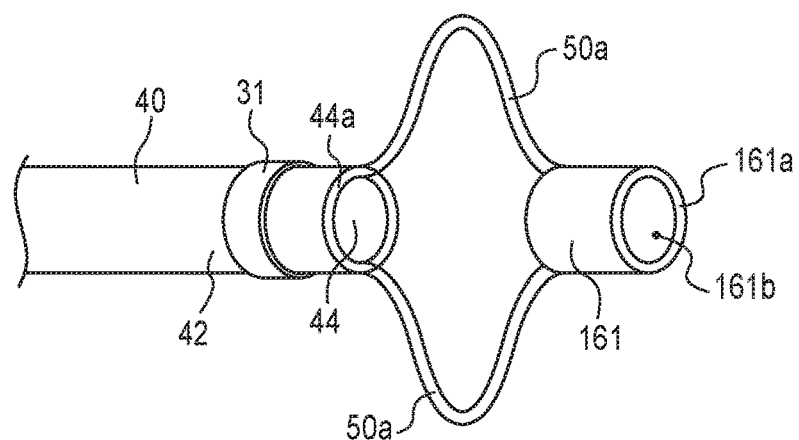
FIG. 20 is a perspective view of a proximal end portion of yet another embodiment of the proximal member that is usable with the stent of FIG. 1.
Figure 21:
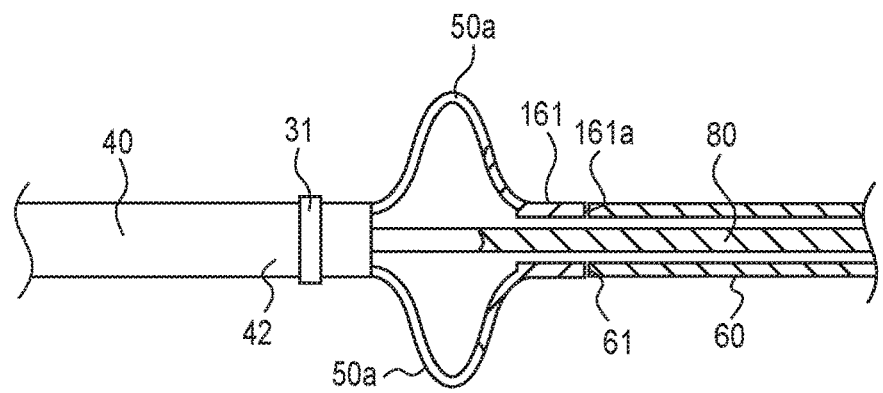
FIG. 21 is a side view of the proximal end portion of FIG. 20, with a collar that is sized such that the first pusher cannot yet extend therethrough with an end face of the first pusher engaging an end face of the collar.
Figure 22:
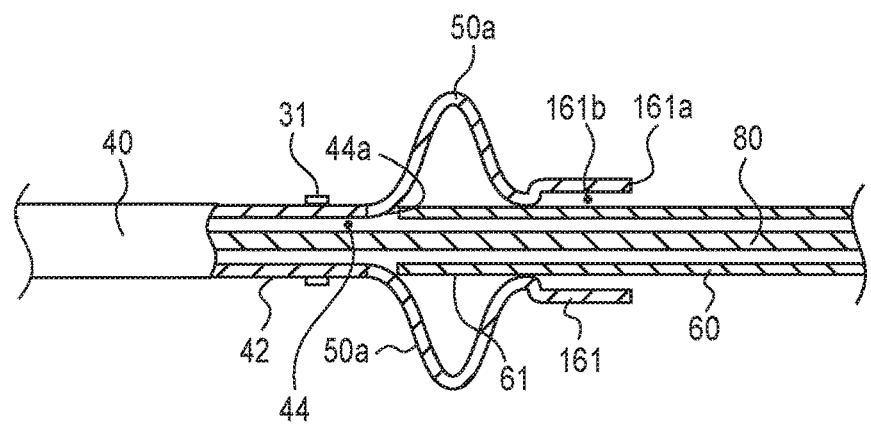
FIG. 22 is a side view of the proximal end portion of FIG. 20, with a collar that is sized such that the first pusher can extend therethrough, with an end face of the first pusher engaging a proximal end face of the proximal member of the stent.

In some embodiments depicted in FIGS. 20-22, the malecot may include a collar 161 that is disposed at the proximal end of each malecot arm 50a and aligns all of the malecot arms 50a together. In some embodiments as shown in FIG. 22, the collar 161 may include an inner diameter is larger than the outer diameter of the first pusher 60 to allow the first pusher 60 (discussed below) to extend through the collar 161 and therefore contact the proximal end face 44a of the proximal member 40. In other embodiments as shown in FIG. 21, the collar 161 may have an inner diameter that is smaller than the outer diameter of the first pusher 60, such that the end face of the first pusher 60 contacts the proximal end face 161a of the collar 161. In embodiments where the collar and (and the arms 50a) are constructed from the same material(s) as the proximal member 40 (such as by removing material from the proximal member 40 to form the voids between the arms 50a) the collar may be expanded radially outward to a larger diameter than the proximal end portion 42 of the proximal member 40, which increases the diameter of the lumen 161b, which may allow the first pusher 60 to extend through the lumen 161b and ultimately contact the proximal end face 44a of the second member 40. In other embodiments, the collar 161 may be a separate component that is attached to the malecot arms 50a (or may be an assembly that includes the malecot arms 50a) such that the collar 161 may be formed initially such that the diameter of its lumen 161b is larger than the outer diameter of the first pusher 60 to allow the first pusher 60 to extend therethrough to contact the proximal end face 44a of the second member 40 of the stent.

In some embodiments, it may be preferred to configure the collar 161 with a lumen 161b with a diameter that is larger than the than the outer diameter of the first pusher 60, so that the first pusher 60 may interact with the proximal end face 44a proximal member 40 (and not the collar 161 and malecot arms 50a) so that the length of the stent may be adjusted when at least a portion of the proximal member 40 and the malecot arms 50a are disposed within the urethra. FIGS. 20-22 depict a malecot device with two arms 50a that extend from opposite sides of the proximal end portion 42, while in other embodiments, the collar 161 may be fixed to a malecot device with a differing number of arms, such as 3, 4, 5, or 6. For example, embodiments with 4 arms, the 4 armed device may be constructed similarly to the device depicted in FIG. 1 and discussed above, with the collar 161 connected to the end of each of the four arms (or in embodiments with a differing number of arms 50a, the end of each arm 50a).

In still other embodiments the enlarged portion 50 may be shaped like a funnel or a cone, with a small end of the funnel or cone fixed to the proximal end portion 42 at a connection point 53 and the larger portion of the funnel or cone extending radially (and longitudinally) away from the connection point 53. The funnel or cone 50b, 50c may be sized with a largest portion that extends to a radial distance within the ranges for the arms 50a discussed above, and similar design constraints and objectives may apply to the funnel or cone 50b, 50c as apply to the arms 50a.

Figure 10:
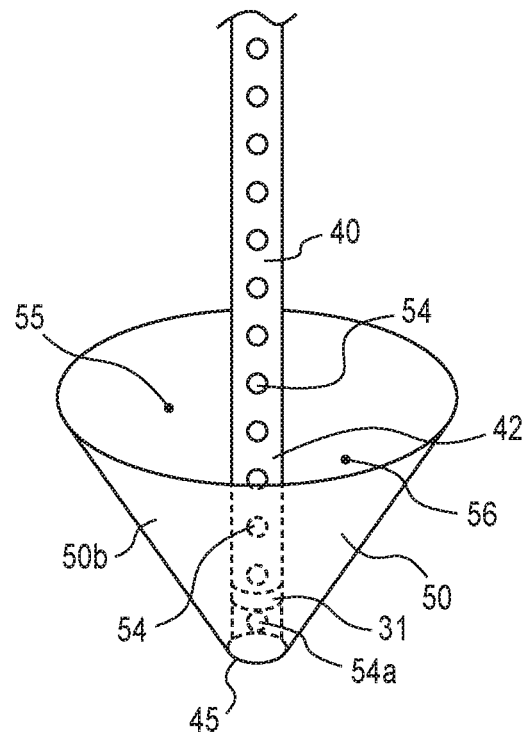
FIG. 10 is a view of a proximal end portion of another embodiment of the proximal member that is usable with the stent of FIG. 1.
Figure 11:
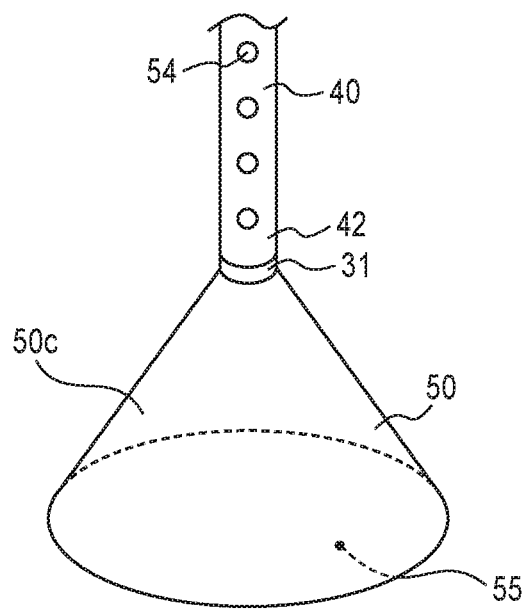
FIG. 11 is a view of a proximal end portion of yet another embodiment of the proximal member that is usable with the stent of FIG. 1.
Figure 12:
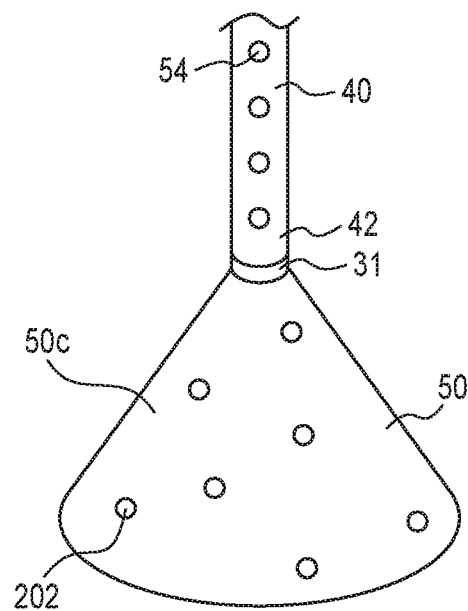
FIG. 12 is a view of a proximal end portion of yet another embodiment of the proximal member that is usable with the stent of FIG. 1.
Figure 13:
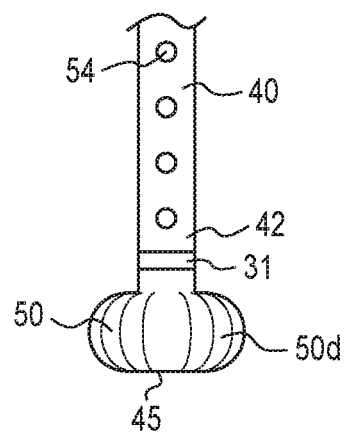
FIG. 13 is a view of a proximal end portion of yet another embodiment of the proximal member that is usable with the stent of FIG. 1.

As shown in FIG. 10, the funnel 50b may be formed with an opening 55 that faces distally, and as shown in FIG. 11, the funnel 50c may be formed with an opening 55 that faces proximally. In some embodiments, the funnel 50b, 50c may formed by a continuous material, while in other embodiments, the funnel 50b, 50c may be formed with a plurality of apertures 202, as shown in FIG. 12. The funnel 50b, 50c may be formed such that it is biased toward a radially extended position, which includes a larger diameter in one or more directions or portions than the UVJ and ureter, but may be compressed to a configuration just larger than the outer surface 47 of the remainder of the proximal end portion 42 to allow for advancement and removal through the urethra.

Figure 14:
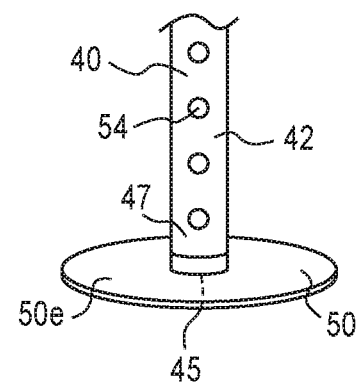
FIG. 14 is a view of a proximal end portion of yet another embodiment of the proximal member that is usable with the stent of FIG. 1.

In still other embodiments shown in FIG. 14, the enlarged portion 50 may be a flat plate or disc 50e, i.e. a structure that extends generally only radially from the outer surface 47 of the proximal end portion 42, and includes at least one diameter or portion that is larger than the UVJ, and is collapsible to a configuration just larger than the outer surface 47 of the remainder of the proximal end portion 42. The disc 50e may extend radially to a diameter within the range for the arms 50a discussed above, and the same design constraints may apply to the disc as discussed with respect to the arms 50a, above. In embodiments with a bulb 50d, the bulb 50d may extend to an outer profile or diameter that is within the ranges identified above with respect to the size of the malecot arms 50a and many of the same design constraints may apply to the bulb 50d. Additionally, because the bulb 50d may not be completely (or even partially) compressible when before or during deployment, the outer diameter or cross-section of the bulb 50d may be the smallest size that would not extend within the UVJ that is available. One of ordinary skill would understand what sizes of bulbs were available without undue experimentation with a thorough review and understanding of this specification.

In still other embodiments, the enlarged portion 50 of the proximal end portion 42 may be a portion that is biased into an arcuate shape, such as a pigtail (similar in shape to the arcuate distal end portion 21 of the distal member 20 depicted in FIG. 1), or other arcuate structure mentioned with respect to the distal end portion 21 of the distal member 20, above. The formation of the enlarged portion 50 that is biased into an arcuate configuration assists with preventing the stent 10 from moving distally into the ureter after deployment.

Figure 27:
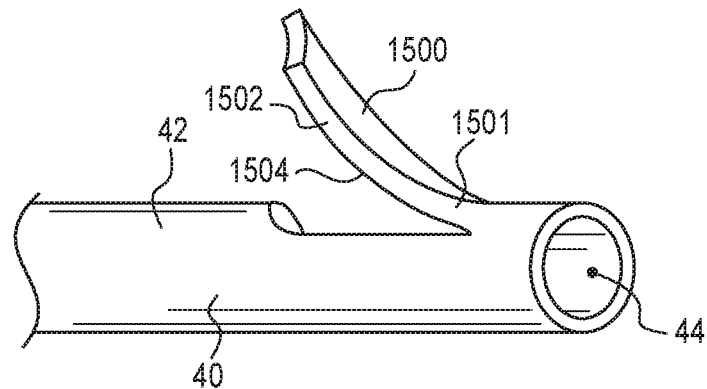
FIG. 27 is a perspective view of a proximal end portion of the proximal member that is usable with the stent of FIG. 1, with in an extended position.
Figure 28:
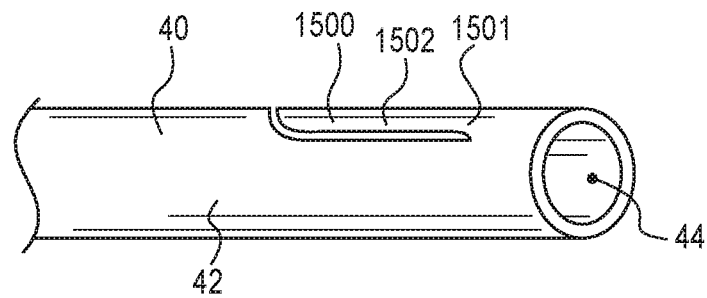
FIG. 28 is the view of the embodiment of FIG. 27 in an inline position.

In still other embodiments as shown in FIGS. 27-28, the proximal end portion 42 of the proximal member may include an enlarged portion 1500 that is formed from a section of the wall that includes a fixed portion 1501 that is attached to the proximal end portion 42 and a free portion 1502 that is biased to extend radially outward from the outer wall of the proximal end portion 42 (FIG. 27). The free portion 1502 may be straight along its length (between its tip and the fixed portion 1501) or in other embodiments the free portion 1502 may be curved along its length. In embodiments where the free portion 1502 is curved, the curve may be such that a convex surface 1504 of the curve faces the UVJ and the ureter when deployed. In some embodiments, the free portion 1502 may have a curved cross-section along a portion or the entire length of the free portion. The curved cross-section may match the circumference of the remaining portion of the proximal end portion 42 of the proximal member 40, or it may be another profile.

The free portion 1502 may be biased to extend radially away from the outer wall of the proximal end portion 42. The biasing force may be from a spring, an imbedded wire (such as a superelastic wire that is trained or oriented to bias outward), or by the design of the material forming the free portion 1502. The free portion 1502 is configured such that it can be urged against the radially outward biasing force to a profile where the free portion 1502 is substantially in-line with the remaining outer surface of the proximal end portion 42 of the proximal member (FIG. 28). The free portion 1502 may be configured such that when the proximal member is withdrawn proximally (i.e. to remove the stent from the patient) the free portion 1502 may contact the urethral sphincter (or other transition surfaces between the bladder and the urethra), which urges the free portion 1502 toward the in-line position to allow the proximal member 40 to be withdrawn from the patient through the urethra without damaging the walls of the urethra. In some embodiments, a single free portion 1502 may be provided. Other embodiments, two or potentially more similar free portions 1502 may be provided that extend radially outward in different directions and from different circumferential positions of the proximal end portion 42.

In some embodiments, engagement between the distal end portion 41 (and specifically the tip 43 of the distal end portion 41) of the proximal member 40 and the distal member 20 (either the proximal end portion 22 or a central portion disposed between the distal and proximal end portions 21, 22) is configured to cause a longitudinal force placed on the proximal member 40 in the proximal direction (direction P, FIG. 1) to be transferred to the distal member 20 to cause the distal member 20 to slide proximally within the patient along with the proximal member 40. This engagement may be beneficial to allow the distal member to be removed from the ureter (and kidney) by pulling only on the proximal member 40 when a deployed stent 10 is desired to be removed.

Figure 8:
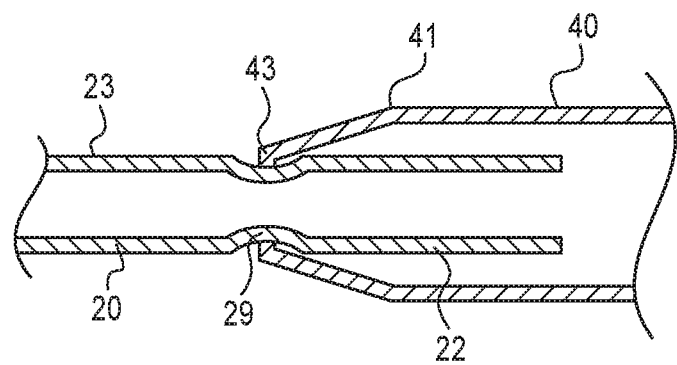
FIG. 8 is a detail view of one embodiment of an indwelling stent depicting engagement between the distal tip of the proximal member and the outer surface of the distal member, showing localized compression of the distal member.

As shown in FIG. 8, the distal tip 43 of the proximal member 40 (and in some embodiments an additional portion of the distal end portion 41 proximal of the distal tip 43) may be configured with an inner diameter (or at least an inner diameter in one direction or portion) that is less than a nominal outer diameter of the distal member 20 along the proximal end portion 22 and the central portion 29, such that the interaction between the distal tip 43 and the outer surface 23 of the distal member locally compresses the distal member 20. The local compression of the distal member 20 and the engagement with at least the distal tip 43 causes a high amount of friction therebetween, which at least substantially prevents unintended relative longitudinal movement between the distal and proximal members 20, 40, such as when the stent 10 is deployed through a patient's ureter. Additionally, the high frictional contact between the distal tip 43 of the proximal member 40 and the distal member 20 causes a proximal longitudinal force that is applied to the proximal member 40 to be transferred to the distal member 20 to urge the distal member 20 to slide out of the kidney, through the ureter, and ultimately out of the patient when clinically desired.

In some embodiments, the distal tip 43 (and in some embodiments other portions of the distal end portion 41 that engages and locally compresses the distal member 20) may be manufactured to be harder or stiffer than the distal member 20 such that the distal member 20 is locally deformed when engaged by the distal tip 43. The distal tip 43 may be made from a harder material that the distal member 20, and/or the distal tip 43 may be made to be harder or stiffer than the distal member 20 with a harder or stiffer material connected with or embedded within the distal tip 43.

Figure 9:
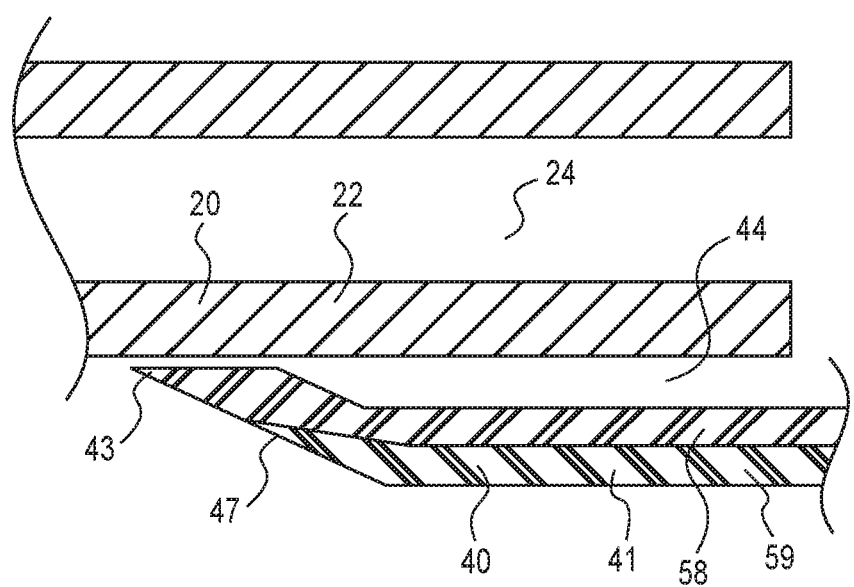
FIG. 9 is a detail view A of FIG. 2, showing a detailed cross-sectional view of the distal end portion of one embodiment of the proximal member.

In still other embodiments shown in FIG. 9, the proximal member 40, or in some embodiments, the distal tip 43 and other portions of the distal end portion 41 that contact the outer surface 23 of the distal member 20 is formed from a first material 58 that defines the inner surface forming the lumen 44 and a second material 58 that defines the outer surface of at least a portion of the proximal member 40. The first material 58 may be a material that is harder, or has a higher coefficient of friction than the second material 59, with the high coefficient of friction of the first material 58 providing a high frictional contact between the distal tip 43 and associated portions of the distal end portion 41 of the proximal member that contacts the distal portion 20. This high frictional contact prevents or resists unintended sliding between the distal and proximal end portions 20, 40, which assists with maintaining the stent 10 positioned as desired within the patient when deployed, and also may allow for a proximal force applied to the proximal member 40 to be transferred to the distal member 20 to withdraw both members of the stent 10 from the patient. In some embodiments, the second material 59 may be provided (coaxially or otherwise) around the first material 58 at the distal tip 43 and in some embodiments proximally of the distal tip 43, while in other embodiments, the distal tip 43 may be only the first material, but may include stiffeners that are attached to or embedded into the distal tip 43.

In some embodiments, the proximal member 40 may be formed as a co-extruded tube with the first and second materials co-extruded to form the proximal member 40. In some embodiments, the first material may be one of various composites of high density polyethylene (HDPE) of low density polyethylene (LDPE), polyurethane, or other thermoplastics (including composites of multiple of these materials, or composites of one or more of these materials along with another material). The second material 59 may be a material listed above (or a composite of the materials listed above, or a composite of a material listed above and other material), but may be formed with a lower coefficient of friction than composites of the first material to achieve the differences in friction discussed above. In other embodiments, the first and second materials may be made from other materials, which will be understood to be appropriate by those of skill in the art after a thorough review and understanding of this specification.

In other embodiments shown in FIG. 2, a proximal tip 28 of the proximal end portion 22 of the distal member 20 may be formed with an enlarged portion 28, such as a bulge, that is larger than an inner diameter or at least one section of at least the distal tip 43 of the proximal member 40. As can be appreciated with review of FIG. 2, in these embodiments, when the proximal member 40 is urged in the proximal direction P, the distal tip 43 eventually engages the enlarged portion 28, which allows a proximal force applied to the proximal member 40 to be transferred to the distal member 20 to urge the distal member 20 to slide proximally with the proximal member 40.

In some embodiments, the distal tip 43 of the proximal member 40 may be formed to locally compress the distal member 20 in addition to the enlarged portion 28 being provided on the proximal tip 37 of the distal member. In some embodiments, one or both of these features may also be provided with the flexible member 120 being threaded through an aperture 32 in the distal member 20, as discussed below. One of ordinary skill will comprehend with a review and understanding of this disclosure that one, some, or all of these features may be provided to assist with removing the stent 10, and specifically the distal member 20 from the patient.

In some embodiments, one or both of the distal end portion 21 of the distal member 20 and the proximal end portion 42 of the proximal member 40 may include a portion (30, 31, respectively, FIG. 1, such as an echogenic or radiopaque portion or another surface that is visible indirectly) that is configured to be visible with indirect vision of a patient's anatomy, such as through fluoroscopy or through ultrasound, or another indirect vision technology. The benefits of these portions 30, 31 are discussed with respect to the deployment procedure of the stent 10, discussed below, as well as to allow the stent 10 to be noninvasively confirmed to be correctly positioned within a patient after deployment. In some embodiments, the distal end 61 of the first pusher 60 (discussed below) may also be provided with an indirect vision portion 63 (such as echogenic or radiopaque) that allows the position of the proximal tip 45 of the proximal member 40 to be observed based upon the position of the distal end 61 of the first member 60, which may be provided in parallel with or without the portion 31 on the proximal member 40. In some embodiments, one or both of the distal end portion 21 of the distal member 20 and the distal end portion 41 of the proximal member 40 may include a transition portion 25, 48 that extends proximally from the tip of the respective distal end portion 21, 41. The transition portion 25, 48 may provide a gradual increase in the outer diameter of the respective distal end portion to minimize trauma to the anatomy when the respective portion of the stent 10 is advanced distally. The transition could be a conical shape, as shown with respect to the transition portion 48 (FIGS. 1, 2), or the transition could be a curved shape, as shown with respect to the distal tip 25 of the distal member 20.

Figure 4:
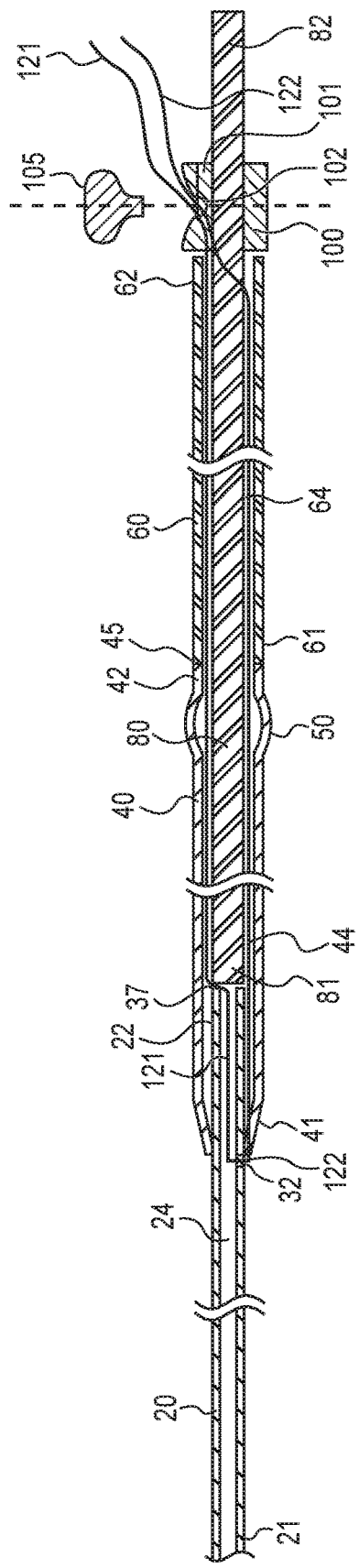
FIG. 4 is a cross-sectional view of the system of FIG. 3.

As best shown in FIGS. 1 and 4, in some embodiments, the distal member 20 may include a side hole 32 that is adapted to receive a flexible member 120 therethrough. The flexible member 120 may be a suture, a string, a thread, or a monofilament, or another material that is strong in tension when at a very small cross-section. The flexible member 120 extends between a first portion 121 that extends into the stent 10 though the proximal member 40 lumen and through a portion of the distal member lumen 24 and extends outside of the lumen 24 through the side hole 32. The second portion 122 of the flexible member 120 extends along the outer surface 23 of the distal portion 20 and extends through the distal tip 43 and into the lumen 44 of the proximal member 40, and ultimately extends out of the proximal member 40. In some embodiments, the first and second portions 121, 122 of the flexible member 120 are each of a sufficient length to extend out of the patient (and normally out of the patient's ureter) when the stent 10 is properly positioned. In embodiments were the stent 10 is deployed with a delivery system, such as the delivery system 300 discussed below, the first and second portions 121, 122 of the flexible member 120 are long enough to extend out of a lumen 64 of the first pusher 60 and engage the lock 100 disposed upon the second pusher 80.

In some embodiments, and as shown in FIG. 1, the distal member 20 includes a plurality of apertures 34 that are disposed through a side wall of the distal member 20. The plurality of apertures 34 may be distributed along the entire length of the distal member 20, with consistent or inconsistent spacing, and at various circumferential positions about the side wall of the distal member 20.

The proximal member 40 may additionally include a plurality of apertures 54 that are disposed through a side wall of the proximal member 40. The plurality of apertures 54 may be distributed along the entire length of the proximal member 40, with consistent or inconsistent spacing, and at various circumferential positions about the side wall of the proximal member 40. In some embodiments, the plurality of apertures 54 along the proximal member 40 may be formed with a larger size (and formed as circles or other shapes) than the apertures 34 along the distal member 20. In other embodiments, the apertures 34, 54 may be the same shape and size, but the proximal apertures 54 may be positioned more frequently and in closer spacing than the distal apertures 34 such the proximal member 40 forms a collective opening size that is a larger area per unit length than a collective opening size of the distal member 20 per unit length.

In one representative embodiment, the plurality of apertures 54 may each include a diameter within a range of about 0.040 to about 0.060 inches in diameter (inclusive of all diameters within this range), and in some embodiments at a diameter of about 0.050 inches. In some embodiments, the plurality of apertures 54 may be positioned at a spacing of about 5 mm longitudinally between centers of adjacent apertures 54, with adjacent apertures rotating about a circumference of the proximal member 40 in either 45 degree (or 30, 60, 75, or 90) degree increments to form a spiral pattern along the length of the proximal member 40. In some embodiments, a double spiral pattern may be formed, with apertures 54 formed on opposite sides of the proximal member 40. In this or other embodiments, the plurality of apertures 34 along the distal member 20 may each include a diameter within in a range of about 0.030 inches to about 0.040 inches (inclusive of all diameters within this range), and in some embodiments the apertures 34 may be 0.038 inches. The apertures 34 may be arranged about 1 cm apart longitudinally along the distal member 20 and oriented in a spiral pattern with 90 degree spacing circumferentially between adjacent apertures 34. Other spacing and distribution may be used as well. In other embodiments, the plurality of apertures 54 on the proximal member 40 may be the same size and spacing of the apertures 34 on the distal member 20, discussed above.

It will be appreciated by one of ordinary skill with a thorough review of the subject specification that the larger proximal openings 54 (or a larger collective opening size per unit length), such as openings that are formed with the larger individual or collective opening size per unit length may be clinically beneficial to prevent adverse effects of reflux of urine from the bladder and into the ureter that has been clinically noted with conventional ureteral stents.

As can be understood, the presence of a ureteral stent extending through a patient's UVJ into a patient's bladder may allow urine to backflow into the ureter, in addition to patients that exhibit VUR (vesicoureteral reflux) or other clinical problems when the UVJ does not prevent the backflow of urine into the ureter. The backflow of urine into the ureter may be most prevalent in areas of the ureter between the inner surface of the ureter and the outer surface 47 of the stent 10, due to capillary action exhibited into the relatively small spaces outside of the stent 10. The larger openings 54 (or collective opening area) on the proximal member 40 allow for urine to easily flow between the ureter and the stent 10, and with flow (with little resistance or head loss) into the lumen 44 of the proximal member 40 and then flow back into the bladder, as the path of least resistance for flow.

In embodiments discussed above with a funnel 50*b*, 50*c* or a disc 50*e* on the proximal end portion 42 of the proximal member 40, the funnel or disc may include a plurality of holes 202 (FIG. 12) that allows urine to flow through the funnel or planar portion and into the bladder from the ureter. In embodiments where the funnel or disc 50*b*, 50*c*, 50*e* does not include the holes 202, the plurality of apertures 54 upon the proximal member 40 may be formed to extend all of the way, or almost all of the way to the proximal tip 45 of the proximal member 40, such that any urine that collects within the internal volume 56 of the funnel 50*b* (or collects above the disc 50*e*) will drain through lowest one or more apertures 54 and through the lumen 44 of the proximal member 40 into the bladder.

Figure 3:
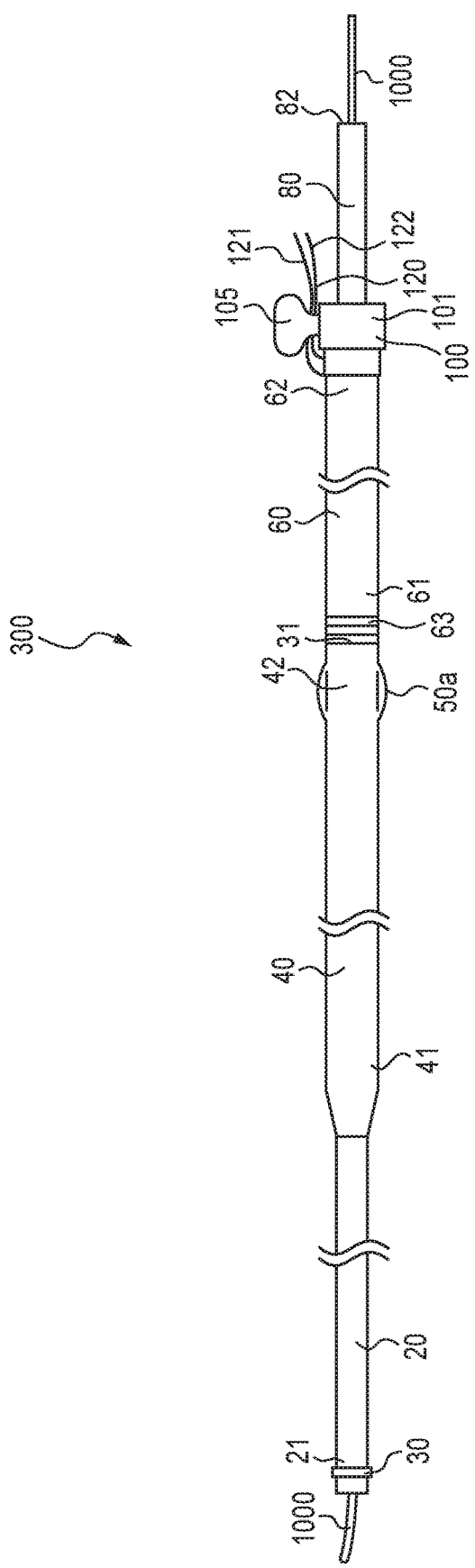
FIG. 3 is a side view of a system for deploying the indwelling stent of FIG.

Turning now to FIGS. 3 and 4, the stent 100 may be deployed within a patient with a delivery system 300. The delivery system 300 may include a first pusher 60 that extends between distal and proximal ends 61, 62 and includes a lumen 64 therethrough. The system 300 may further include a second pusher 80 that is disposed through the lumen 64 of the first pusher 60 and extends between distal and proximal tips 81, 82. The second pusher 80 may support a lock 100, discussed elsewhere herein.

As best shown in FIG. 4, the distal tip 81 of the second pusher 80 is in close proximity or in contact with the proximal tip 37 of the first member 20, and the first pusher 60 is aligned such that the distal end 61 of the first pusher 60 is in close proximity or in contact with the proximal tip 45 of the second member 40. The second pusher 80 may be significantly longer than the first pusher 60 and the proximal end portion of the second pusher 80 extends proximally out of the first pusher 60.

The first and second pushers 60, 80 are each configured such that the pushers are slidable with respect to each other, and each configured with a sufficient column strength such that a distal longitudinal force applied to one of the pushers 60, 80 is transferred to the respective first or second member 20, 40 of the stent 10 to cause the respective member to move distally within the patient's anatomy.

When the delivery system 300 is assembled with the stent 10, the first and second portions 121, 122 of the flexible member 120, discussed above, may be threaded through the lumen 64 of the first pusher after leaving the lumen 44 of the second member 40. Both portions of the flexible member 120 that leave the lumen 64 of the first pusher are normally retained with respect to the second pusher 80 with the lock 100, discussed below. In other embodiments, one or both of the first and second portions 121, 122 of the flexible member 120 may extend from the proximal member 40 of the stent 10 to the lock 100 along the outer surface of the first pusher 60.

A first embodiment of a lock 100 is depicted in FIGS. 3 and 4. The lock 100 may include a fixed portion 101 that is fixed (directly or indirectly) to the second pusher 80 in a position where the lock 100 does not interfere with distal motion of the first pusher 60 with respect to the second pusher 80 needed for deployment or positioning of the stent 10 within the patient. The lock 100 further is configured to maintain the distal member 20 in place with respect to the second pusher 80 when engaged, therefore maintaining the stent 10 and the delivery system 300 connected during deployment and final positioning within the ureter.

The fixed portion 101 may include a slot, aperture, or similar structure 102 that is configured to receive the first and second portions 121, 122 of the flexible member 120 therethrough. The lock 100 may additionally include a removable portion in 105 that is removably engaged with the fixed portion 101, and the removable portion 105 is configured such that the flexible member 120 that is extended through the structure 102 of the fixed portion 101 is prevented from being radially or longitudinal moved with respect to the fixed portion 101. When the removable portion 105 is removed from the fixed portion 101, the first and or second portions 121, 122 can be radially or longitudinally removed from the slot, aperture or similar structure 102. As can be understood, the removal of the flexible member 120 from the lock 100 allows for the second pusher 80 and the first pusher 60 to be removed from the patient after the stent 10 is properly deployed.

Figure 23A:
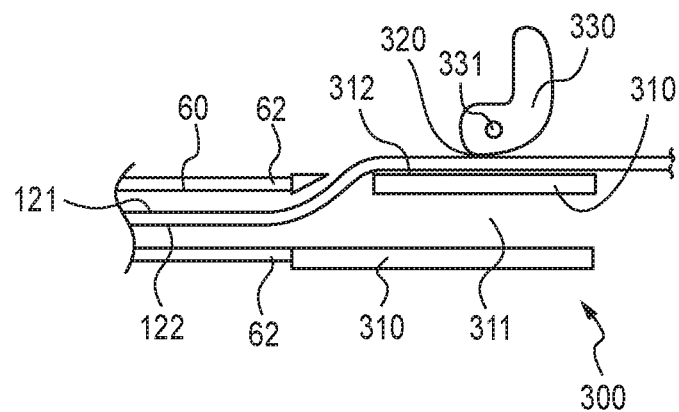
FIG. 23a is a side view of a lock that is usable to selectively retain and release a flexible member associated with the distal member of the stent, with the lock disengaged from the flexible member.
Figure 23B:
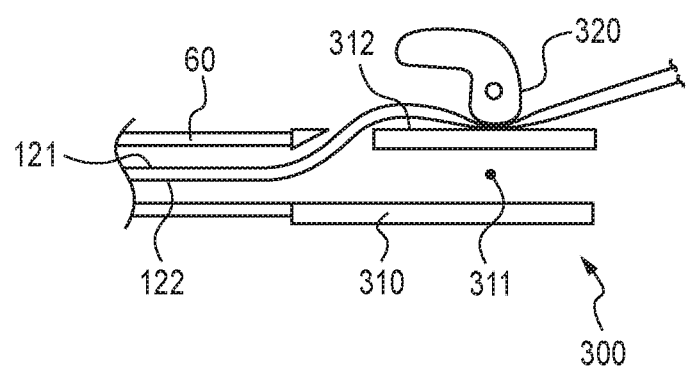
FIG. 23b is the view of FIG. 23a with the lock engaged with the flexible member.

In other embodiments shown in FIGS. 23*a*-23*b*, another lock 300 may be provided to selectively retain the first and second portions 121, 122 of the flexible member 120. The lock 300 may fixed (directly or indirectly) with the second pusher 80. The lock 300 may be associated with the lock 200 (discussed below, which removably fixes the first and second pushers 60, 80 together), or with another mechanism to perform this functionality. The lock 300 may include a housing 310 with a lumen 311 to receive the first and second portions 121, 122 therethrough, such as through the lumen of the first pusher 60, when connected thereto.

The housing 310 supports a lever 330 that pivots (and in some embodiments may be retained) between a locking position (FIG. 23b) that engages the first and second portions 121, 122 to prevent their relative movement with respect to the housing 310 and a release position (FIG. 23a) where the lever 330 does not engage the first and second portions 121, 122 and therefore allows for relative movement, such as pulling the portions 121, 122 with respect to the housing 310. The lever 330 may be pinned to the housing 310 with a pin 331 to allow the lever 330 to freely pivot. The lever 330 may include a cam surface 320 (or another outer surface) that has a varying profile (such as an outer surface with a varying radius from the pin 331, such that the position of the cam surface 320 changes when the position of the lever 330 changes, and the cam surface 320 engages the outer surface 312 of the housing when in the locking position thereby also pressing upon the first and second portions 121, 122 (when provided therebetween) and preventing their movement with respect to the housing 310. When the lever 330 is pivoted to the release position the cam surface 320 disengages the outer surface 312 of the housing and therefore removes the pressing force upon the first and second portions 121, 122 to allow for their relative movement.

In some embodiments, the lever may be an "over center" design that is urged toward both the locking and release positions after passing through a midpoint where there is no biasing force. In other embodiments, the lever may be urged toward one or both of the locking and release positions with a spring or other biasing member. The lever 330 is depicted herein as pointing radially away from the remaining portions of the lock 300 when in the release position, and relatively parallel to the proximal end portion 42 when in the locking position. One of ordinary skill in the art will understand after the thorough review of this specification and drawings that the lever 330 may be oriented and shaped in virtually any desired direction for either position, such as may be dedicated by ergonomic factors (i.e. to allow the physician to hold and manipulate the lever 330 with a single hand.).

Figure 24:
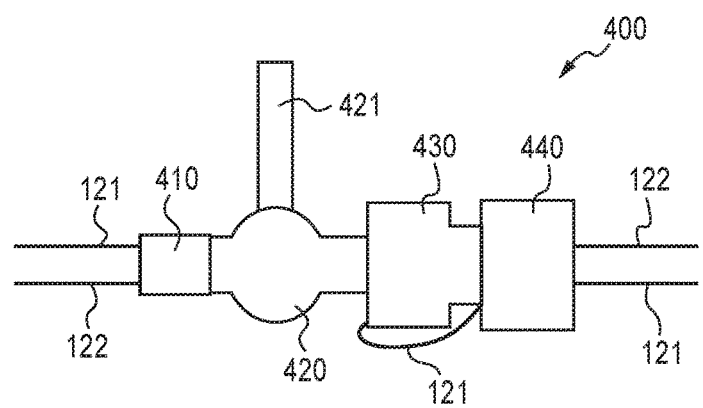
FIG. 24 is side view of a lock that is usable to selectively retain and release one or both portions of a flexible member associated with the distal member of the stent.
Figure 25:
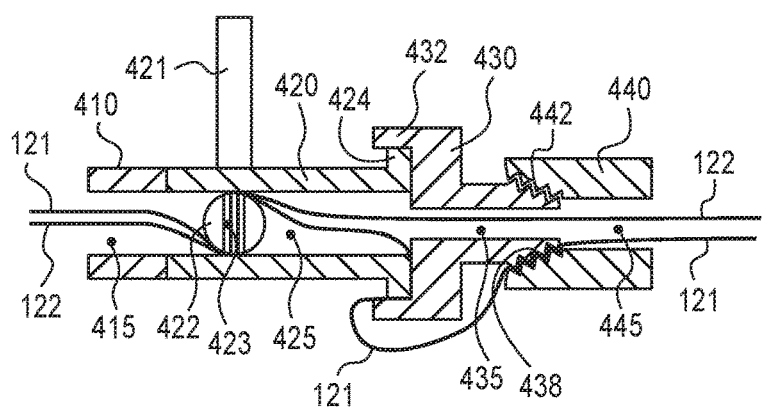
FIG. 25 is a cross-sectional view of the lock of FIG. 24 depicting both portions of the flexible member retained by the lock.
Figure 26:
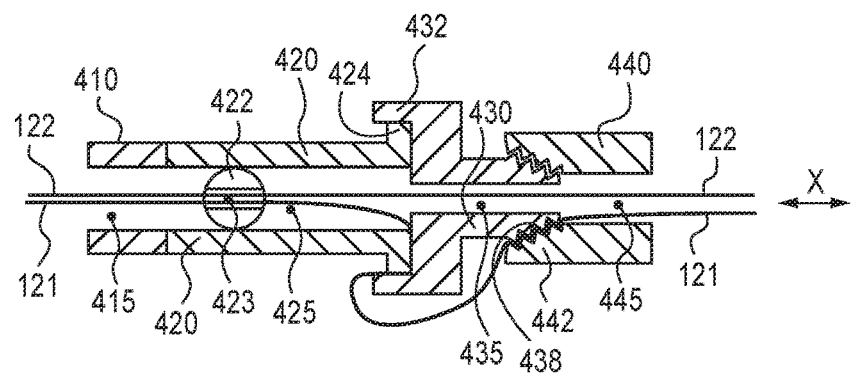
FIG. 26 is the view of FIG. 26 depicting one portion (122) of the flexible member released by the lock, such that the portion may translate with respect to the lock in the direction X, and a second portion (121) retained by the lock.

In other embodiments depicted in FIGS. 24-26, another lock 400 for the maintaining the flexible member 120 in position is provided. The lock 400 may be fixed (directly or indirectly) with the second pusher 80. Specifically, the lock 400 may selectively retain both of the first and second portions 121, 122, and may in other configurations selectively retain only one of the first and second portions 121, 122 (the element 121 is depicted as retained in FIG. 26, but can be the opposite), while allowing the other to be released (i.e. pulled with respect to the lock 400 and the remaining portions of the device). This lock 400 may be preferred in situations where the flexible member 120 is desired to be removed from the patient after the stent is deployed. The lock 400 may include a base 410 that allows the lock 400 to be fixed to another portion of the device, such as directly to the first pusher 60, or to another portion of the lock, such as lock 200 discussed below. The base 410 may be fixed to a valve 420 that can be manipulated between a locking position (FIG. 25) and a release position (FIG. 26). The valve 420 may be a ball valve (as depicted) or a gate valve, or other type of valve known in the art.

In embodiments that include a ball valve, the valve 420 may include an operator 421 that is fixed to a rotatable ball 422 disposed within the body of the valve 420. The ball includes a port 423 that can be oriented in an "inline" position (FIG. 26) that allows unimpeded movement through the port (such as by the flexible member 120). FIG. 26 depicts the lock 400 without the operator 421 for simplicity purposes, but if depicted the operator 421 may be parallel to the body of the valve (i.e. horizontal on the page per the view of the figure) but the operator may be sized and shaped into another ergonomic position (as well as size and shape) in either position of the valve 420.

The ball 422 can be rotated by the operator 421 to a "blocking" position (FIG. 25) that establishes a tortuous path for passage into and through the port 423, which prevents movement of the flexible member with respect to the valve. The valve may include a locking structure 424 at the proximal end, such as a leer lock or a threaded member. In other embodiments, a lever (such as the lever 330), a structure similar to the removable portion 105, above, or another structure may be provided to selectively retain and release the flexible member 120 extending therethrough may be provided instead of the valve 420.

A fitting 430 may be selectively fixed to the locking structure, specifically with a complementary structure 432 to the locking structure 424 of the valve 420. In some embodiments, one of the first or second portions 121, 122 (121 in the figure for simplicity) of the flexible element 120 may extend between the corresponding locking and complementary structures 428, 432 to fix the position of the portion therebetween when engaged. The other of the first and second portions 121, 122 may extend through the lumens 425, 435 of both the valve and the fitting 430. In some embodiments, the opposite end of the fitting 430 may include a second locking structure such as a threaded portion 438 (depicted in FIGS. 25 and 26), which may be engaged with a complementary threaded portion 442 of a nut 440. In embodiments where the nut 440 is threadably attached, the first portion 121 may also be disposed between this threaded connection for further support, and the second portion may be threaded through the lumen of the nut 440. In some embodiments, the first portion 121 may be wrapped once or multiple times around the threaded portion 438 to provide an effective lock of the first portion 121 when the nut is attached to the threaded portion 438.

As discussed further below, after the distal and proximal members 20, 40 of the stent have been positioned, the first and second pushers 60, 80 may then be withdrawn from the patient. If the flexible member is also desired to be removed, the physician would position the valve 420 to the inline position, which releases the hold of one of the two portions of the flexible member (122 depicted in FIGS. 25 and 26) while retaining the other portion (121 in the figures) fixed to the luer and/or threaded connections (420, 430, 440), such that when the inner positioner 80 is withdrawn from the patient, fixed end of the suture (121) is pulled. This pulling ultimately removes the flexible member from the side hole 32 in the distal member 20 of the stent and ultimately removes the entire flexible member 120 from the patient.

In embodiments, where the physician wishes to retain the flexible member within the patient after deployment, the physician may both switch the valve 420 to the inline position and also remove the fitting 430 from the luer 428, and when provided remove the nut 440 from the fitting 430, which releases the other end of the flexible member. Then, when the inner member is withdrawn from the patient, which also withdraws the components of the lock 400, the flexible member 400 is retained in place. In embodiments where the flexible member is to be retained within the patient after deployment, the two ends of the first and second portions 121, 122 of the flexible member 120 may be tied or otherwise connected to maintain the flexible member extending through the side hole 32 in the distal portion 20.

Figure 15:
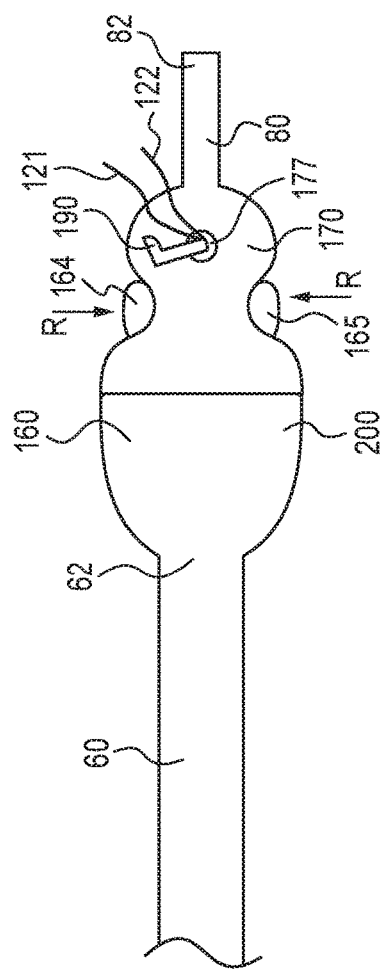
FIG. 15 is a top view of a lock that may be provided with the delivery system used with the stent of FIG. 1, with the first and second components of the lock engaged.
Figure 16:
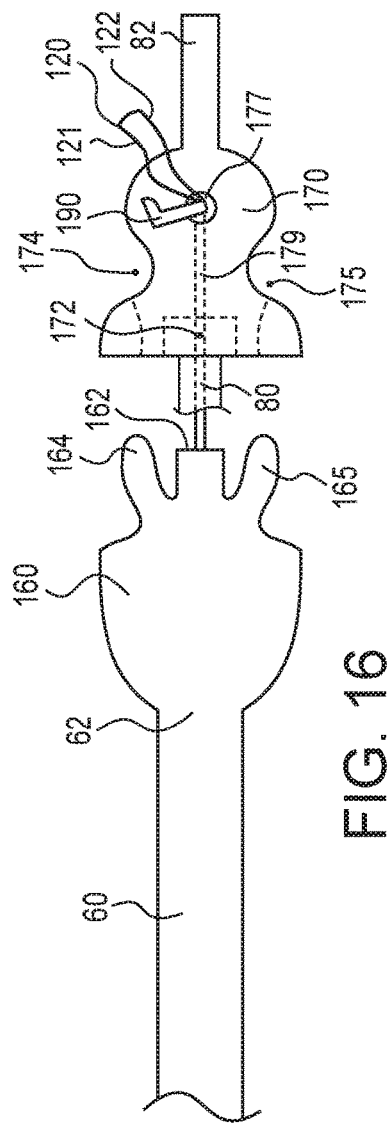
FIG. 16 is the view of the lock of FIG. 15 with the first and second components of the lock disengaged.

Turning now to FIGS. 15-16, an alternate lock 200 may be provided to removably fix the first and second pushers 60, 80 together (and therefore also fix the distal and proximal members 20, 40 of the stent to the delivery system 300) may be provided. The lock 200 includes a first component 160 that is fixed to the first pusher 60 and a second component 170 that is fixed to the second pusher 170, with the first and second components being engagable to fix the first and second pushers 60 80 together. In some embodiments, the first component 160 may be a male component with one or more arms 164, 165 that are flexible and biased toward engagement with structure in the second component 170. The second component 170 may include a plurality of voids or spaces 174, 175 that are configured to receive the respective arms 164, 165 when the first and second components 160, 170 are coupled together. The arms 164, 165 may be biased to extend into the respective voids 174, 175, but may be released from the voids when desired, such as by pressing each arm 164, 165 radially inwardly in the direction R (or in another direction as needed) to withdrawn the arms 164, 165 from the voids to allow the first and second couplers 160, 170 to be decoupled.

In some embodiments, the first coupler 160 is formed with an opening 162 that is in communication with the lumen 63 of the first pusher 60 to allow the second pusher 80 to slide therethrough. In some embodiments, first and second components may have mating surface (parallel or otherwise) to allow for close contact therebetween, and may have one or more structural features to strengthen the connection therebetween, and to provide alignment features to prevent relative slippage or rotation therebetween, such as surfaces with mating flats, keys and keyways, selective pins and mating holes, etc.

The second component 170 may include a side (or end) port 177 that receives a removable pin 190, a re-positionable lever, or another structure that when positioned can engage the first and second portions 121, 122 of the flexible member 120, which when positioned (in the engaged position) further prevents relative motion between the first and second components 160, 170, and additionally prevents relative longitudinal movement of the distal member 20 of the stent 10 with respect to the first and second pushers 60, 80, thereby maintaining the stent 10 and delivery system 300 together as a unit during deployment and telescopic positioning of the proximal member 40 with respect to the distal member 20. The pin 190 or other structure is configured to be removable or repositionable (to the release position) to no longer engage the first and second portions 121, 122 of the flexible member 120, thereby allowing the first and second couplers 160, 170 to be decoupled, and the first and second pushers 60, 80 to be removed from the stent 10 when positioned within the patient.

A method of deploying an indwelling stent 10 will be understood with reference to the stent 10 and the delivery system 300 discussed herein. Initially, a wire guide 1000 may be advanced through the urethra, bladder, ureter, and into the patient's kidney using known techniques. The method discussed herein may be practiced with a scope disposed into the patient's bladder, with the UVJ being observed through the scope.

After the wire guide 1000 is properly positioned, the stent 10 and the delivery system 300 are backloaded onto the portion of the wire guide 1000 that extends out of the patient, and the stent 10 and delivery system 300 are threadably advanced through the patient's urethra, bladder, and into the appropriate ureter through the UVJ, with a distal end portion 21 of the distal member 20 of the stent 10 ultimately entering into the kidney. In embodiments where the distal end portion 21 of the distal member 20 includes an indirectly visible portion 30 (such as an echogenic or radiopaque band) the proper position of the distal end portion 21 of the distal portion 20 can be indirectly observed with ultrasound, fluoroscopy, or via another known method. The stent 10 and delivery system 300 are normally positioned such that the proximal end portion 42 of the proximal member 40 extends into the bladder when the distal end portion 21 of the distal member 20 extends into the kidney.

Once the correct position of the distal member 20 is verified within the kidney and the ureter, the wireguide 1000 may be proximally withdrawn from the distal end portion 21, which allows the distal end portion 21 to move toward its normal arcuate orientation, such as a pigtail, a helix, or the like, which causes the distal member 20 to be maintained within the kidney.

When the correct position of the distal member 20 is verified, the proximal member 40 is advanced distally within the ureter to decrease the overall length of the stent 10, by sliding the first pusher 60 distally over the second pusher 80. The engagement between the distal end 61 of the first pusher 60 and the proximal tip 45 of the proximal member 40 and the distal force placed upon the first pusher 60 urges the proximal member 40 distally such that the proximal member 40 telescopically covers more of the distal member 20 as the proximal member 40 is urged distally (reducing the overall length of the stent 10). In embodiments where a collar 161 that supports the malecot arms 50a is provided, the pusher 60 extends through the collar 161 to engage the proximal tip 45, or in embodiments where the inner diameter of the collar 161 is smaller than the outer diameter of the first pusher 60, the distal end 61 of the first pusher 60 engages the proximal face 161a of the collar 160, and force applied to the collar 161 is transferred to the proximal member 40 through the malecot arms 50a.

The proximal member 40 is continued to be urged distally (optionally under the direct vision through the scope and supplemented by the indirect observation of the indirectly visible portion 31 on the proximal end portion 42 of the proximal member 40, when provided) until the enlarged portion 50 of the proximal member 40 engages or comes into close contact with the UVJ. In some embodiments, a sheath or other structure may be provided to temporarily compress the enlarged portion 50 for initial deployment, and the sheath is removed from the enlarged portion 50 just before the proximal member 40 is advanced toward the UVJ to allow for the enlarged portion to engage the UVJ.

The correct position of the proximal member 40 may be directly and/or indirectly verified. Next, in embodiments where a flexible member 120 and a lock 100, 200, 300, 400 are provided, the lock 100, 200, 300, 400 is disengaged from the suture, by manipulating the structure of the locks 100, 200, 300, 400 discussed with respect to the embodiments of the locks, above. After the lock is disengaged, the one or both portions 121, 122 of the flexible member of the flexible member may be disengaged from the lock and the second pusher 80 can then be pulled proximally out of the patient. As discussed above, if portions 121, 122 are disengaged from the lock, the flexible member 120 is retained within the patient (and the ends of the portions may be tied to be retained during prolonged insertion of the stent) after the second pusher 80 is withdrawn from the patient. If only one portion 121, 122 of the flexible member is disengaged and the other portion remains engaged (FIG. 26) the removal of the inner member (and lock) will ultimately remove the flexible member from the side hole 32 in the distal member 20 of the stent as well as from the patient. The first pusher 60 may then be pulled proximally out of the patient.

At the end of the deployment procedure, in embodiments where the flexible member 120 is provided, the flexible member is optionally maintained out of the patient, or may be withdrawn or cut based upon clinical preference.

After the stent 10 has been deployed for the desired time, the stent 10 may be removed from the patient as described here. In embodiments where the flexible member 120 (and specifically the first and second portions 121, 122 extend from the patient), the stent 10 may be withdrawn from the patient by pulling on the flexible member 120 proximally. The proximal force on the flexible member 120 is transferred to the distal member 20, due to the threading of the flexible member 120 through the side hole 32 in the distal member 20. The proximal member 40 may be removed from the patient, with a forceps or grasper to engage the proximal member 40 and pulls it proximally. In some embodiments, a sheath may be threaded over the enlarged portion 50 of the proximal end portion 42 to reduce the diameter of the enlarged portion 50.

The disclosure includes the following numbered paragraphs:

Numbered Paragraph 1: An indwelling stent, comprising: a distal member that extends between a distal end portion and a proximal end portion and defines a lumen therethrough, and a proximal member that extends between a distal end portion and a proximal end portion and defines a lumen therethrough, wherein the distal member and the proximal member collectively define the stent and the lumen of the distal member and the lumen of the proximal member are each aligned for direct communication through both lumens between the distal end portion of the distal member and the proximal end portion of the proximal member, and wherein the distal and proximal members are discrete components and are telescopingly arranged.

Numbered Paragraph 2: The indwelling stent of numbered paragraph 1, wherein the distal end portion of the distal member is biased into an arcuate configuration, and can be straightened with a wire guide disposed through the lumen of the distal member.

Numbered Paragraph 3: The indwelling stent of numbered paragraph 1, wherein the proximal end portion of the proximal member comprises an enlarged portion that extends radially to a larger diameter in at least one direction than an outer diameter of the distal end portion of the proximal member.

Numbered Paragraph 4: The indwelling stent of numbered paragraph 3, wherein the proximal end portion of the proximal member includes a plurality of malecot arms that are collectively biased into a diameter that is larger than the outer diameter of the distal end portion of the proximal member.

Numbered Paragraph 5: The indwelling stent of numbered paragraph 4, wherein the plurality of malecot arms collectively extend to a collar that is disposed proximally of a proximal end face of the proximal member, wherein the collar comprises a lumen that allows communication of an elongate member through the lumen to contact the proximal end face of the proximal member.

Numbered Paragraph 6: The indwelling stent of numbered paragraph 3, wherein the proximal end portion of the proximal member includes a conical portion with an outer diameter that is larger than the outer diameter of the distal end portion of the proximal member.

Numbered Paragraph 7: The indwelling stent of numbered paragraph 3, wherein the proximal end portion of the proximal member includes a bulbous portion with an outer diameter that is larger than the outer diameter of the distal end portion of the proximal member.

Numbered Paragraph 8: The indwelling stent of numbered paragraph 1, wherein a tip of the distal end portion of the proximal member has an inner diameter that is less than a nominal outer diameter of the proximal end portion of the distal member, such that the tip of the distal end portion of the proximal member locally compresses the distal member at a location where the tip contacts the distal member.

Numbered Paragraph 9: The indwelling stent of numbered paragraph 1, wherein a proximal end of the proximal end portion of the distal member includes an enlarged portion that is formed with an outer diameter that is greater than an inner diameter of a tip of the distal end portion of the proximal member.

Numbered Paragraph 10: The indwelling stent of numbered paragraph 1, wherein each of the distal end portion of the distal member and a proximal end portion of the proximal member include a portion that is configured to be visible with indirect vision of a patient's anatomy.

Numbered Paragraph 11: The indwelling stent of numbered paragraph 1, wherein the distal end portion of the proximal member includes a transition portion that gradually and continuously extends between a first diameter at a tip of the distal end portion and a larger second diameter proximal of the tip.

Numbered Paragraph 12: The indwelling stent of numbered paragraph 1, wherein the distal member further comprises a hole disposed through a side wall of the distal member, and the stent further includes a length of an elongate flexible member that extends through the hole, wherein a portion of the elongate flexible member extends through the lumen of the proximal member and a proximal portion of the lumen of the distal member and through the hole, and a second portion of the flexible member extends along an outer surface of the distal member past the proximal end portion and through the lumen of the proximal member.

Numbered Paragraph 13: The indwelling stent of numbered paragraph 12, further comprising a lock disposed proximal of the proximal member, wherein the lock is configured to receive the first and second portions of the flexible member and prevent relative movement of the flexible member with respect to the distal and proximal members when the lock receives the flexible member.

Numbered Paragraph 14: The indwelling stent of numbered paragraph 3, wherein the enlarged portion of the proximal end portion of the proximal member may be urged to an outer diameter that is substantially the same as an outer diameter of a remaining portion of the proximal member.

Numbered Paragraph 15: The indwelling stent of numbered paragraph 1, wherein the distal end portion of the proximal member extends over an outer surface of the distal member for a portion of a length of the distal member.

Numbered Paragraph 16: The indwelling stent of numbered paragraph 1, wherein the proximal member is slidable about an outer surface of the distal member, wherein the relative position of the proximal member with respect to the distal member controls a total length of the stent between a distal tip of the distal member and a proximal tip of the proximal member.

Numbered Paragraph 17: The indwelling stent of numbered paragraph 1, wherein the distal member has a plurality of first apertures disposed through a side wall along a length of the distal member and the proximal member has a plurality of second apertures disposed through a side wall along a length of the proximal member, wherein a size of each of the plurality of second apertures is larger than a size of each of the plurality of first apertures.

Numbered Paragraph 18: The indwelling stent of numbered paragraph 1, wherein the distal member has a plurality of first apertures disposed through a side wall along a length of the distal member that collectively form a first opening size along the first member, and the proximal member has a plurality of second apertures disposed through a side wall along a length of the proximal member that collectively form a second opening size along the second member, wherein the second opening size is a larger area per unit length of the proximal member than the first opening size per unit length of the distal member.

Numbered Paragraph 19: The indwelling stent of numbered paragraph 1, wherein the proximal member is formed from a first material that forms an inner surface of the lumen through the proximal member and a second material that forms an outer surface of the proximal member, wherein the first material has a higher coefficient of friction than the second material.

Numbered Paragraph 20: A system of deploying an indwelling stent, comprising: a distal member that extends between a distal end portion and a proximal end portion and defines a lumen therethrough, and a proximal member that extends between a distal end portion and a proximal end portion and defines a lumen therethrough, wherein the distal member and the proximal member collectively define the stent, and the lumen of the distal member and the lumen of the proximal member are each aligned for direct communication through both lumens between the distal end portion of the distal member and the proximal end portion of the proximal member, and wherein the distal and proximal members are discrete components and are telescopingly arranged, a first pusher that extends between distal and proximal ends with a lumen therethrough, and a second pusher that extends between a distal tip and proximal tip and is disposed through the lumen of the first pusher and the lumen of the proximal member with the distal tip of the second pusher contacting the proximal end portion of the distal member.

Numbered Paragraph 21: The system of numbered paragraph 20, wherein with the distal end portion of the proximal member extends over the outer surface of the distal member for a portion of a length of the distal member.

Numbered Paragraph 22: The system of numbered paragraph 20, wherein the proximal tip of the second pusher extends out of the lumen of the first pusher and the first pusher is longitudinally movable with respect to the second pusher.

Numbered Paragraph 23: The system of numbered paragraph 20, wherein the distal member further comprises a hole disposed through a side wall of the distal member, and the stent further includes a length of an elongate flexible member that extends through the hole, wherein a first portion of the elongate flexible member extends through the lumen of the proximal member and a proximal portion of the lumen of the distal member, and a second portion of the flexible member extends along an outer surface of the distal member past the proximal end portion and through the lumen of the proximal member.

Numbered Paragraph 24: The system of numbered paragraph 23, further comprising a lock fixed with the second pusher, wherein the lock is configured to receive the first and second portions of the flexible member, and the lock may be positioned in a locking configuration that prevents relative movement of the flexible member with respect to the distal and proximal members.

Numbered Paragraph 25: The system of numbered paragraph 23, wherein the lock comprises a lever that is configured to be positioned to engage the first and second portions of the flexible member to prevent their motion with respect to the lock, and the lever is additionally movable to a second position to remove the engagement with the first and second portions.

Numbered Paragraph 26: The system of numbered paragraph 23, wherein the lock comprises a first portion that selectively fixes and selectively releases a position of the first and second elements, and a second portion that is configured to selectively engage and release one of the first or second elements, such that the first or second element not engaged by the second portion may be translated with respect to the lock when the first portion releases the first and second elements.

Numbered Paragraph 27: The system of numbered paragraph 26, wherein each of the first and second portions of the lock are configured to be independently disposed into a locking arrangement to fix the first or second element disposed therewith and to be independently released from the locking arrangement to release the first or second element disposed therewith.

Numbered Paragraph 28: The system of numbered paragraph 26, wherein the first element is a valve and the second element is a threaded connection between correspondingly threaded members.

Numbered Paragraph 29: The system of numbered paragraph 20, wherein the proximal end portion of the proximal member comprises an enlarged portion that extends radially to a larger diameter than an outer diameter of the distal end portion of the proximal member.

Numbered Paragraph 30: The system of numbered paragraph 20, wherein the proximal member is slidable about an outer surface of the distal member, wherein the relative position of the proximal member with respect to the distal member controls a total length of the stent between a distal tip of the distal member and a proximal tip of the proximal member.

Numbered Paragraph 31: The system of numbered paragraph 20, wherein each of the distal end portion of the distal member and a proximal end portion of the proximal member include a portion that is configured to be visible with indirect vision of the anatomy Numbered Paragraph 32: The indwelling stent of numbered paragraph 20, wherein a tip of the distal end portion of the proximal member has an inner diameter that is less than a nominal outer diameter of the proximal end portion of the distal member, such that the tip of the distal end portion of the proximal member locally compresses the distal member at a location where the tip contacts the distal member.

Numbered Paragraph 33: The indwelling stent of numbered paragraph 20, wherein the proximal end portion of the distal member includes a bulge that is formed with an outer diameter that is greater than an inner diameter of a tip of the distal end portion of the proximal member.

While the preferred embodiments have been described and illustrated in detail, it is to be understood that this is intended by way of illustration and example only, the scope of the invention being limited by the terms of the following claims.

The invention claimed is:

1. An indwelling stent, comprising:
a distal member that extends between a distal end portion and a proximal end portion and defines a lumen therethrough, the distal member forms an outer surface that establishes an outer diameter, the distal member extends to a proximal tip on the proximal end portion, and a proximal member that extends between a distal end portion and a proximal end portion and defines a lumen therethrough that establishes an inner diameter of the proximal member, wherein the distal member and the proximal member collectively define the stent and the lumen of the distal member and the lumen of the proximal member are each aligned for direct communication through both lumens between the distal end portion of the distal member and the proximal end portion of the proximal member, and wherein the distal and proximal members are discrete components and are telescopingly arranged such that at least a portion of the proximal end portion of the distal member is disposed within the lumen of the proximal member,
wherein the proximal tip of the proximal end portion of the distal member includes an enlarged portion that is formed with an outer diameter that is greater than an inner diameter of a tip of the distal end portion of the proximal member and is greater than the outer diameter of the distal end portion and remaining proximal end portion of the distal member.

2. The indwelling stent of claim 1, wherein the distal end portion of the distal member is biased into an arcuate configuration, and can be straightened with a wire guide disposed through the lumen of the distal member.

3. The indwelling stent of claim 1, wherein the proximal end portion of the proximal member comprises an enlarged portion that extends radially to a larger diameter in at least one direction than an outer diameter of the distal end portion of the proximal member.

4. The indwelling stent of claim 3, wherein the proximal end portion of the proximal member includes a plurality of malecot arms that are collectively biased into a diameter that is larger than the outer diameter of the distal end portion of the proximal member.

5. The indwelling stent of claim 4, wherein the plurality of malecot arms collectively extend to a collar that is disposed proximally of a proximal end face of the proximal member, wherein the collar comprises a lumen that allows communication of an elongate member through the lumen to contact the proximal end face of the proximal member.

6. The indwelling stent of claim 3, wherein the proximal end portion of the proximal member includes a conical portion with an outer diameter that is larger than the outer diameter of the distal end portion of the proximal member.

7. The indwelling stent of claim 3, wherein the proximal end portion of the proximal member includes a bulbous portion with an outer diameter that is larger than the outer diameter of the distal end portion of the proximal member.

8. The indwelling stent of claim 1, wherein a tip of the distal end portion of the proximal member has an inner diameter that is less than a nominal outer diameter of the proximal end portion of the distal member, such that the tip of the distal end portion of the proximal member locally compresses the distal member at a location where the tip contacts the distal member.

9. The indwelling stent of claim 1, wherein each of the distal end portion of the distal member and a proximal end portion of the proximal member include a portion that is configured to be visible with indirect vision of a patient's anatomy.

10. The indwelling stent of claim 1, wherein the distal end portion of the proximal member includes a transition portion that gradually and continuously extends between a first diameter at a tip of the distal end portion and a larger second diameter proximal of the tip.

11. The indwelling stent of claim 1, wherein the distal member further comprises a hole disposed through a side wall of the distal member, and the stent further includes a length of an elongate flexible member that extends through the hole, wherein a portion of the elongate flexible member extends through the lumen of the proximal member and a proximal portion of the lumen of the distal member and through the hole, and a second portion of the flexible member extends along an outer surface of the distal member past the proximal end portion and through the lumen of the proximal member.

12. The indwelling stent of claim 11, further comprising a lock disposed proximal of the proximal member, wherein the lock is configured to receive the first and second portions of the flexible member and prevent relative movement of the flexible member with respect to the distal and proximal members when the lock receives the flexible member.

13. The indwelling stent of claim 3, wherein the enlarged portion of the proximal end portion of the proximal member may be urged to an outer diameter that is substantially the same as an outer diameter of a remaining portion of the proximal member.

14. The indwelling stent of claim 1, wherein the distal end portion of the proximal member extends over an outer surface of the distal member for a portion of a length of the distal member.

15. The indwelling stent of claim 1, wherein the proximal member is slidable about an outer surface of the distal member, wherein the relative position of the proximal member with respect to the distal member controls a total length of the stent between a distal tip of the distal member and a proximal tip of the proximal member.

16. The indwelling stent of claim 1, wherein the distal member has a plurality of first apertures disposed through a side wall along a length of the distal member and the proximal member has a plurality of second apertures disposed through a side wall along a length of the proximal member, wherein a size of each of the plurality of second apertures is larger than a size of each of the plurality of first apertures.

17. The indwelling stent of claim 1, wherein the distal member has a plurality of first apertures disposed through a side wall along a length of the distal member that collectively form a first opening size along the first member, and the proximal member has a plurality of second apertures disposed through a side wall along a length of the proximal member that collectively form a second opening size along the second member, wherein the second opening size is a larger area per unit length of the proximal member than the first opening size per unit length of the distal member.

18. The indwelling stent of claim 1, wherein the proximal member is formed from a first material that forms an inner surface of the lumen through the proximal member and a second material that forms an outer surface of the proximal member, wherein the first material has a higher coefficient of friction than the second material.

* * * * *